(12) United States Patent
Imai et al.

(10) Patent No.: US 9,109,043 B2
(45) Date of Patent: Aug. 18, 2015

(54) SCREENING METHOD FOR ANTIDIABETIC AGENT USING NEWLY IDENTIFIED INSULIN SECRETION REGULATION FACTOR

(75) Inventors: Takeshi Imai, Yokohama (JP); Hiroshi Handa, Yokohama (JP)

(73) Assignee: Tokyo Institute of Technology, Tokyo (JP)

( * ) Notice: Subject to any disclaimer, the term of this patent is extended or adjusted under 35 U.S.C. 154(b) by 0 days.

(21) Appl. No.: 13/819,809

(22) PCT Filed: Sep. 2, 2011

(86) PCT No.: PCT/JP2011/070067
§ 371 (c)(1),
(2), (4) Date: Jun. 10, 2013

(87) PCT Pub. No.: WO2012/029958
PCT Pub. Date: Mar. 8, 2012

(65) Prior Publication Data
US 2013/0288959 A1 Oct. 31, 2013

(30) Foreign Application Priority Data
Sep. 2, 2010 (JP) .................................. 2010-196952

(51) Int. Cl.
*C07K 14/47* (2006.01)
*A61K 38/45* (2006.01)
*A61K 38/16* (2006.01)
*A01K 67/027* (2006.01)

(52) U.S. Cl.
CPC .......... *C07K 14/4703* (2013.01); *A01K 67/0275* (2013.01); *A61K 38/16* (2013.01); *A61K 38/45* (2013.01); *A01K 2217/052* (2013.01); *A01K 2227/105* (2013.01); *A01K 2267/0362* (2013.01); *G01N 2500/00* (2013.01); *G01N 2800/042* (2013.01)

(58) Field of Classification Search
None
See application file for complete search history.

(56) References Cited

FOREIGN PATENT DOCUMENTS

EP 2583693 A1 4/2013
WO 0112845 A1 2/2001

OTHER PUBLICATIONS

Bonzo et al. FASEB. 2006;20:A265.*
Uniprot. UGGG1_Mouse. 2014.*
Trubetskoy et al. ASSAY and Drug Development Technologies. 343-354;5(3):2007.*
Arnold, S.M. et al., "The noncatalytic portion of human UDP-glucose: glycoprotein glucosyltransferase I confers UDP-glucose binding and transferase function to the catalytic domain," J.Biol.Chem., 2003, vol. 278, p. 43320-43328.
Pearse, B.R. et al., "The role of UDP-Glc: glycoprotein glucosyltransferase 1 in the maturation of an obligate substrate prosaposin," J.Cell.Biol., May 2010, Vo.189, p. 829-841.
Ohtsubo, K. et al., "Dietary and genetic control of glucose transporter 2 glycosylation promotes insulin secretion in suppressing diabetes," Cell, 2005, vol. 123, p. 1307-1321.
Hiramoto, M. et al., "High-performance affinity chromatography method for identification of L-arginine interacting factors using magnetic nanobeads," Biomed.Chromatogr., Jun. 2010, vol. 24, p. 606-612.
"PCT International Search Report dated Oct. 31, 2011 for PCT/JP2011/070067, from which the instant application is based," 2 pgs.
Bonzo, J. et al., "Transgenic UDP-glueuronsyltransferase 1 mice are protected from obesity-induced type 2 diabetes," FASEB Journal, vol. 20, No. 1, Part 1, Mar. 2006, p. A265, Abstract.
European Search Report dated Feb. 24, 2014 from related Application No. EP 1182197.2, 7 pgs.

* cited by examiner

*Primary Examiner* — Amber D Steele
*Assistant Examiner* — Schuyler Milton
(74) *Attorney, Agent, or Firm* — Fredrikson & Byron, P.A.

(57) ABSTRACT

It is an object of the present invention to provide a newly identified insulin secretion regulation factor that can control blood sugar in the normal range, and a method for screening an antidiabetic drug using said factor.
In accordance with the present invention, there is provided a composition which is (i) a protein comprising an amino acid sequence represented by SEQ ID NO: 2 or SEQ ID NO: 4; or (ii) a protein comprising an amino acid sequence in which one or several amino acids are deleted, substituted or added in an amino acid sequence represented by SEQ ID NO: 2 or SEQ ID NO: 4 and negatively regulating insulin secretion, as well as a method for screening antidiabetic drug using said protein or a nucleic acid encoding the same.

2 Claims, 7 Drawing Sheets

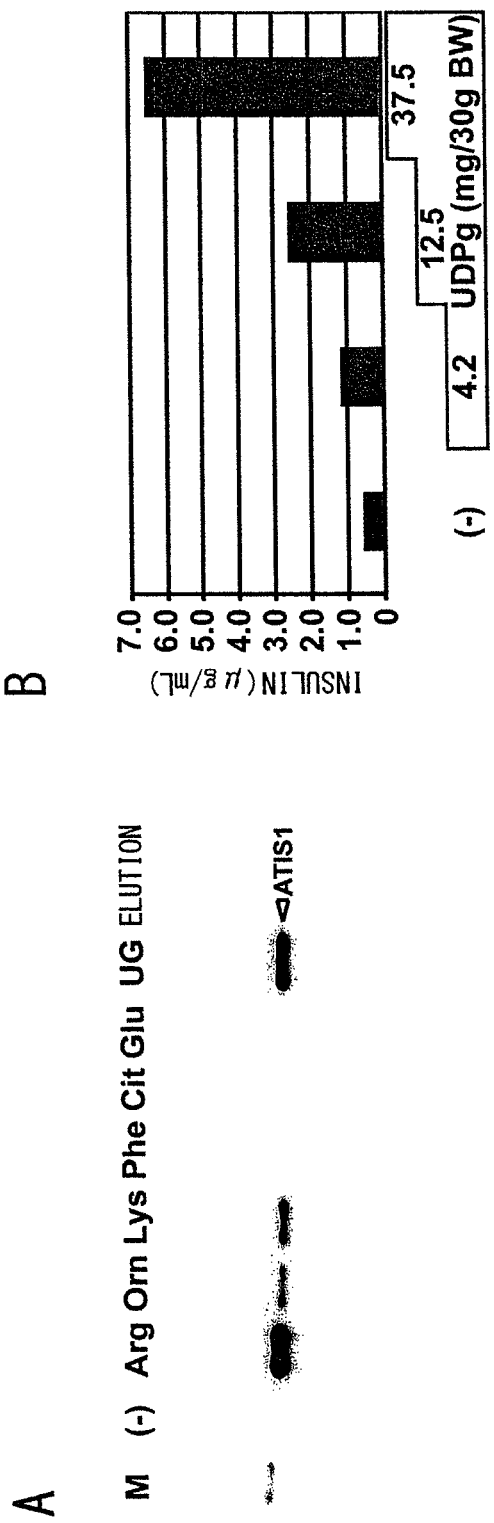

SCREENING METHOD FOR ANTIDIABETIC AGENT USING NEWLY IDENTIFIED INSULIN SECRETION REGULATION FACTOR

RELATED APPLICATIONS

This application is a 35 U.S.C. 371 national stage filing from International Application No. PCT/JP2011/070067 filed Sep. 2, 2011 and claims priority to Japanese Patent Application No. 2010-196952, filed on Sep. 20 2010, the teachings of which are incorporated herein by reference.

TECHNICAL FIELD

The present invention relates to a newly identified insulin secretion regulation factor and a method for screening an antidiabetic drug using said factor.

BACKGROUND ART

Diabetes mellitus is a disorder accompanied by a persistent hyperglycemia, and is said to result from interaction between a variety between environmental factors and genetic factors. Blood sugar is mainly controlled by insulin, and elevated blood sugar is known to result from insulin deficiency or excess of factors (such as genetic disposition, lack of exercise, obesity, and stress) that inhibit the action of insulin. Diabetes mellitus is divided into two types: type I diabetes mellitus caused by the reduced function of insulin secretion due to autoimmune disease, etc., and type II diabetes mellitus caused by the reduced function of pancreatic insulin secretion due to pancreatic fatigue associated with persistently elevated insulin secretion and insulin resistance. In Japan, diabetes mellitus is a national affliction, and more than 95% of the diabetic patients (predicted to exceed 20 million people including diabetic candidates) are said to be non-insulin-dependent diabetes mellitus. The increasing number of patients due to changes in life style is posing a problem. On a global level, the number is expected to be about 200 million (Non-patent document 1), and the global market size of antidiabetics is about one trillion yen, indicating that diabetes mellitus is the number one disease in terms of the market size of its therapeutic agents and the number of population.

The treatment of diabetes mellitus, in mild cases, mainly comprises diet therapy, exercise therapy, amelioration of obesity, etc., and, in more advanced cases, the administration of oral antidiabetics (insulin secretion-promoting drugs) and, in further severe cases, the administration of insulin preparations. As insulin secretion-promoting substances (or insulin secretion-promoting drugs), there are known, in addition to glucose, amino acids (specifically arginine), β-receptor stimulating agents, α-receptor blockers, sulfonyl urea drugs and the like. Among them, sulfonyl urea drugs stimulate pancreatic β cells to promote intrinsic insulin secretion, but the timing and the amount secreted of insulin depend not on blood sugar level but on the timing and dosage of the drug. Thus, as a side effect, hypoglycemia may occur due to the persistent action of the drug (Non-patent document 2). Thus, conventional insulin secretion-promoting drugs and insulin preparations had the above problems. There have been needs therefore for drugs that permit more precise blood sugar control, i.e. drugs that not only decrease blood sugar but can maintain blood sugar in the normal range. For this purpose, simple screening methods are needed in order to obtain substances that are useful as insulin secretion-promoting drugs and insulin preparations.

L-arginine, an amino acid, plays a variety of roles in vivo. For example, it is involved in the control of immunological function, wound healing, hormone secretion, vascular tone, endothelial function, and insulin secretion (Non-patent document 3). L-arginine is a biologically active food-borne compound that mediates a variety of physiological actions. In this connection, a metabolic enzyme that uses L-arginine as a substrate is L-arginine interacting factor (AIF). However, little is known about AIF that directly mediates the physiological actions of L-arginine. The present inventors have so far succeeded in the purification and identification of AIF using L-arginine methyl ester (AME)-immobilized magnetic nanobeads developed by us (Non-patent document 4). While AME, similarly to arginine, promotes insulin secretion as an arginine agonist on the one hand, it inhibits nitrogen monooxide synthase (NOS) as an arginine antagonist similarly to L-nitro-L-arginine-methylester) on the other. Using this AME-immobilized magnetic nanobeads, phosphofructokinase (PFK), RuvB-like 2 (RBL2), and RuvB-like 1 (RBL1) were identified as AIF (Non-patent document 4).

A "protein comprising an amino acid sequence represented by SEQ ID NO: 2" used in the screening method of the present invention is a newly identified insulin secretion regulation factor that was isolated using the above AME-immobilized magnetic nanobeads described in Non-patent document 4. The amino acid sequence per se represented by SEQ ID NO: 2 has been registered to GenBank as NM_198899. However, there have been no reports so far that a protein consisting of an amino acid sequence represented by SEQ ID NO: 2 and a nucleic acid consisting of the base sequence encoding said amino acid sequence described in the present specification are involved in the promotion of insulin secretion.

CITATION LIST

Non-Patent Documents

Non-patent document 1: Stumvoll, M., et al., Lancet, 365, 1333-1346 (2005)

Non-patent document 2: McCrimmon, R. J., et al., Diabete. Metab., 20, 503-512 (1994)

Non-patent document 3: Weinhaus, A. J., et al., Diabetologia, 40, 374-382 (1997)

Non-patent document 4: Hiramoto, et al., Biomed. Chromatogr., 24, 606-612 (2010)

SUMMARY OF THE INVENTION

Technical Problem

The problem of the present invention is to provide a protein that promotes insulin secretion or a fragment thereof and a nucleic acid encoding it, a simple screening method for obtaining a substance that is useful as an antidiabetic drug capable of controlling blood sugar within the normal range, specifically an insulin secretion-promoting drug, and furthermore an antidiabetic drug that contains a substance obtained by said screening method.

Solution to Problem

While a plurality of substances are known to promote insulin secretion as described above, the mechanism of insulin secretion has not been fully analyzed on the molecular level. During the course of studying the mechanism of insulin secretion by arginine which is the most potent insulin secretion-promoting substance, the present inventors have discovered a new factor that regulates insulin secretion. By close examination on the mechanism of insulin secretion via this factor, we have found that this insulin secretion regulation factor is a very useful substance as an analytical tool to further investigate insulin secretion promotion substances, and thereby have completed the present invention.

Thus, the present invention is:

[1] A composition for regulating an insulin secretion, comprising an insulin secretion regulation factor, said factor comprising:
  (i) a protein comprising an amino acid sequence represented by SEQ ID NO: 2 or SEQ ID NO: 4; or
  (ii) a protein comprising an amino acid sequence in which one or several amino acids are deleted, substituted or added in an amino acid sequence represented by SEQ ID NO: 2 or SEQ ID NO: 4 and negatively regulating insulin secretion.

[2] A composition for regulating an insulin secretion, comprising an insulin secretion regulation factor, said factor comprising:
  (i) a nucleic acid comprising the base sequence represented by SEQ ID NO: 1 or SEQ ID NO: 3; or
  (ii) a nucleic acid hybridizing under a stringent condition to a nucleic acid that comprises the base sequence represented by SEQ ID NO: 1 or SEQ ID NO: 3 and encoding a protein that negatively regulates insulin secretion.

[3] The composition according to the above [1] or [2] for screening a drug for treating or preventing diabetes mellitus.

[4] A screening method which comprises selecting a test substance having an activity of binding to insulin secretion regulation factor, based on the activity of the test substance to bind to the insulin secretion regulation factor, as a candidate substance for use in a drug for treating or preventing diabetes mellitus, said method comprising the steps of:
  (a) preparing, as insulin secretion regulation factor, the following protein:
    (i) a protein comprising an amino acid sequence represented by SEQ ID NO: 2 or SEQ ID NO: 4; or
    (ii) a protein comprising an amino acid sequence in which one or several amino acids are deleted, substituted or added in an amino acid sequence represented by SEQ ID NO: 2 or SEQ ID NO: 4 and negatively regulating insulin secretion;
  (b) bringing the test substance into contact with the protein prepared in step (a); and
  (c) selecting the test substance that bound to the protein as a candidate substance for use in a drug for treating or preventing diabetes mellitus.

[5] The screening method according to the above [4], wherein the protein in the above step (a) is (i) a protein consisting of an amino acid sequence represented by SEQ ID NO: 2 or SEQ ID NO: 4; or (ii) a protein consisting of an amino acid sequence in which one or several amino acids are deleted, substituted or added in an amino acid sequence represented by SEQ ID NO: 2 or SEQ ID NO: 4 and negatively regulating insulin secretion.

[6] A screening method which comprises selecting a test substance having an activity of promoting insulin secretion, based on said insulin secretion-promoting activity of the test substance, as a candidate substance for use in a drug for treating or preventing diabetes mellitus, said method comprising the steps of:
  (a) preparing transformed cells that were transformed or homologously recombined on the chromosome with a recombinant vector having integrated therein the following nucleic acid:
    (i) a nucleic acid comprising the base sequence represented by SEQ ID NO: 1 or SEQ ID NO: 3; or
    (ii) a nucleic acid hybridizing under a stringent condition to a nucleic acid that comprises the base sequence represented by SEQ ID NO: 1 or SEQ ID NO: 3 and encoding a protein that negatively regulates insulin secretion;
  (b) bringing the test substance into contact with the transformed cells prepared in step (a) and the non-transformed control cells;
  (c) measuring the amount of insulin secreted in each of the above cells; and
  (d) selecting the test substance that restores the insulin secretion of the above transformed cells relative to the above control cells as a candidate substance for use in a drug for treating or preventing diabetes mellitus.

[7] The screening method according to the above [6], wherein the nucleic acid in the above step (a) is (i) a nucleic acid consisting of the base sequence represented by SEQ ID NO: 1 or SEQ ID NO: 3; or (ii) a nucleic acid hybridizing under a stringent condition to a nucleic acid that consists of the base sequence represented by SEQ ID NO: 1 or SEQ ID NO: 3 and encoding a protein that negatively regulates insulin secretion.

[8] A transformed cell for use in the screening method according to the above [6] or [7].

[9] A screening method which comprises selecting a test substance having an activity of promoting insulin secretion, based on said insulin secretion-promoting activity of the test substance, as a candidate substance for use in a drug for treating or preventing diabetes mellitus, said method comprising the steps of:
  (a) preparing a transgenic animal other than a human which contains or homologously recombined on the chromosome with a recombinant vector having integrated therein the following nucleic acid:
    (i) a nucleic acid comprising the base sequence represented by SEQ ID NO: 1 or SEQ ID NO: 3; or
    (ii) a nucleic acid hybridizing under a stringent condition to a nucleic acid that comprises the base sequence represented by SEQ ID NO: 1 or SEQ ID NO: 3 and encoding a protein that negatively regulates insulin secretion;
  (b) administering the test substance to the transgenic animal prepared in step (a) and a control animal having no such nucleic acid;
  (c) determining blood insulin concentration in each of the above animals; and
  (d) selecting the test substance that restores the insulin secretion of the above transgenic animal relative to the above control animal as a candidate substance for use in a drug for treating or preventing diabetes mellitus.

[10] The screening method according to the above [9], wherein the nucleic acid in the above step (a) is (i) a nucleic acid consisting of the base sequence represented by SEQ ID NO: 1 or SEQ ID NO: 3; or (ii) a nucleic acid hybridizing under a stringent condition to a nucleic acid that consists of the base sequence represented by SEQ ID NO: 1 or SEQ ID NO: 3 and encoding a protein that negatively regulates insulin secretion.

[11] A transgenic animal other than a human for use in the screening method according to the above [9] or [10].

[12] A screening method which comprises selecting a test substance having an activity of inhibiting insulin secretion, based on said insulin secretion-inhibiting activity of the test substance, as a candidate substance for use in a drug for treating or preventing diabetes mellitus, said method comprising the steps of:

(a) preparing a knock-out animal other than a human, said animal being partially or completely inhibited for the expression of a gene encoding the following protein:
   (i) a protein comprising an amino acid sequence represented by SEQ ID NO: 2 or SEQ ID NO: 4; or
   (ii) a protein comprising an amino acid sequence in which one or several amino acids are deleted, substituted or added in an amino acid sequence represented by SEQ ID NO: 2 or SEQ ID NO: 4 and negatively regulating insulin secretion,
(b) administering the test substance to the knock-out animal prepared in step (a) and a control animal not inhibited for the expression of the above gene;
(c) determining blood insulin concentration in each of the above animals; and
(d) selecting a test substance that restores the insulin secretion of the above knock-out animal to normal relative to the above control animal as a candidate substance for use in a drug for treating or preventing diabetes mellitus.

[13] A knock-out animal other than a human for use in the screening method according to the above [12].

With regard to a protein consisting of an amino acid sequence represented by SEQ ID NO: 2, there have been no reports that the amino acid sequence and the nucleic acid sequence published as GenBank NM__198899 in NCBI prior to the filing of this application are an insulin secretion regulation factor. The present inventors are the first to identify that the protein consisting of an amino acid sequence represented by SEQ ID NO: 2 is an insulin secretion regulation factor. Surprisingly, it was found that by the forced expression of the insulin secretion regulation factor of the present invention in cultured cells, the insulin-secreting ability of cultured cells can be negatively regulated. Thus, the present invention intends to provide a very effective tool for screening a drug that promotes insulin secretion by developing such a cell system and a transgenic animal in which the insulin regulation factor has been forcibly expressed.

Advantageous Effects of Invention

A protein (or polypeptide) comprising an amino acid sequence represented by SEQ ID NO: 2 or an amino acid sequence represented by SEQ ID NO: 4, a functionally equivalent altered body or a homologous polypeptide thereof have an activity of regulating insulin secretion. Thus, with this protein, a simple screening method for obtaining a substance useful as an antidiabetic drug (specifically an insulin secretion-promoting drug) that can control blood sugar within the normal range can be constructed. Also, a cell or an animal having introduced therein the above insulin secretion regulation factor for screening, which is a screening tool of the present invention, can be used not only for screening a substance useful as an antidiabetic drug but also in a test for confirming the quality standards of pharmaceutical compositions for treating diabetes mellitus.

BRIEF DESCRIPTION OF DRAWINGS

FIG. 2A shows the ability of a radiolabelled insulin secretion regulation factor to bind to an arginine-immobilized agarose (manufactured by Sigma) and an arginine-immobilized nanobeads. In FIG. 2B, an insulin secretion regulation factor produced by a recombinant *Escherichia coli* and radiolabelled arginine were mixed, then subjected to concentration-dependent competitive inhibition with cold arginine, and the radiolabelled arginine that was disconnected was counted. In FIG. 2C, after mixing a radiolabelled insulin secretion regulation factor with arginine, etc., various concentrations of trypsin were mixed therewith, subjected to partial protein digestion and electrophoresis followed by autoradiography. In FIG. 2D, trypsin in the above C was replaced with chymotrypsin, and then subjected to similar analysis.

FIG. 8A shows the result of interaction between an insulin secretion promotion factor (ATIS1) and an amino acid or a sugar using arginine-immobilized agarose. FIG. 8B shows the result of determining the amount of insulin secreted in response to changes in the concentration of the administered UDP-glucose in wild type B6 mice.

MODE FOR CARRYING OUT THE INVENTION

Figure 1:
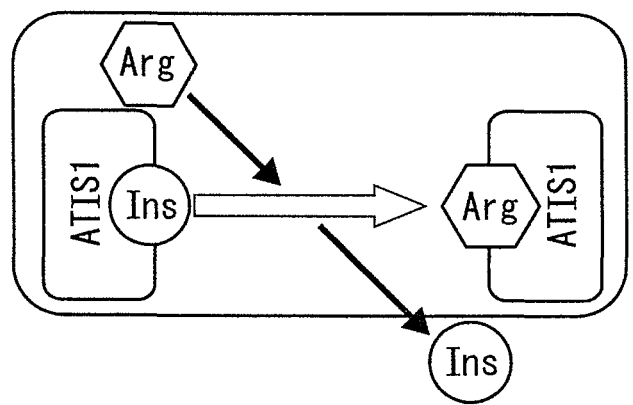
FIG. 1 is a diagram that explains the mechanism of insulin secretion induced by arginine.

The present invention will now be explained in detail below.

1. The Insulin Secretion Regulation Factor of the Present Invention (1-1) Characteristics of the Insulin Secretion Regulation Factor of the Present Invention The insulin secretion regulation factor of the present invention is a protein discovered by the present inventors in the course of investigation on the mechanism of insulin secretion by arginine. First, the present inventors have developed an experimental system for confirming that arginine is a potent factor for insulin secretion. Thus, transformed cultured cells were prepared so as to secrete fluorescently labeled insulin. Using the cells, it was possible to observe insulin secretion by arginine addition and temporal changes in the intracellular localization of insulin with a fluorescent microscope. As a result, it was observed that when arginine was absent in the culture liquid, insulin was present in the periphery of the cell nucleus (at the position of the endoplasmic reticulum), whereas when arginine (10 mM) was added to the culture system, insulin aggregated with each other at 10 seconds after arginine administration, and migrated to the Golgi apparatus at 60 seconds after arginine administration, being extracellularly secreted thereafter resulting in the disappearance of fluorescence (data not shown). The above results suggested that an arginine interacting factor involved in insulin secretion promotion by arginine is present in the endoplasmic reticulum. This experimental system can also be applied to the screening of a candidate substance, other than arginine, that promotes insulin secretion.

Next, using arginine interacting factor-purifying nanobeads (Non-patent document 4) in order to isolate and purify this arginine interacting factor, a novel arginine interacting factor (protein) could be purified and identified from cultured insulin-secreting cells. The amino acid sequence of this arginine interacting factor was found to have a Lys-Asp-Glu-Leu (KDEL)-like sequence (endoplasmic reticulum-localized sequence) at the C-terminal end. Furthermore, by database search, the protein was found to an amino acid sequence identical with an amino acid sequence encoding a known glycosyltransferase (see Pearse, et al., J. Cell Biol. 189, 829-841 (2010)) (see Working Example 1). The amino acid sequence has been registered at GenBank as NM_198899, and in this description, the amino acid sequence of the arginine interacting factor of the present invention is represented by SEQ ID NO: 2 and the base sequence encoding said amino acid sequence is represented by SEQ ID NO: 1. Based on the above base sequence information, an expression vector was constructed and transfected into NIT-1 cells derived from the pancreatic β cells of a non-obese diabetic mouse. The result revealed that this protein is localized in the endoplasmic reticulum (data not shown). Furthermore, as described in Working Example 2 below, the investigation on the regulation of arginine-induced insulin secretion of said protein in NIT-1 cells revealed that this protein has a function of negatively regulating insulin secretion in cultured cells. Protein having a function as described above as an amino acid interacting factor has not been known, and this is a finding discovered by the present inventors for the first time. As used herein, protein having the above characteristics is termed as "insulin secretion regulation factor" (sometimes referred to as "ATIS1" (Arginine Target for Insulin Secretion 1)).

The present invention relates to an insulin secretion regulating composition comprising the above insulin secretion regulation factor. The insulin secretion regulation factor for use in the composition of the present invention is not limited in its origin or method of preparation as long as it has the characteristics described herein. Thus, the insulin secretion regulation factor of the present invention may any of a recombinant protein expressed from DNA by the gene engineering technology or a chemically synthesized protein. Alternatively, it may be a naturally occurring protein instead of an artificially modified one as long as it has the characteristics described herein. Alternatively, it may be a naturally occurring protein that has been modified on the protein level.

The insulin secretion regulation factor of the present invention typically includes, but not limited to, a protein (or polypeptide) comprising an amino acid sequence represented by SEQ ID NO: 2 or an amino acid sequence (corresponding to amino acids 1256-1551 of SEQ ID NO: 2) represented by SEQ ID NO: 4 described in the Sequence Listing. In Working Example 2 described below, in order to examine the characteristics of the insulin secretion regulation factor of the present invention in detail, the arginine-induced insulin secretion ability was compared using cultured cells in which the insulin secretion regulation factor was forcibly expressed and wild type cells in which no forced expression was carried out. As a result, the insulin secretion regulation factor negatively regulated insulin secretion in the cells that had forced-expression, and at an excess amount of arginine, it promoted insulin secretion similarly to the wild type cells (see FIG. 4). Also, it was shown that an insulin secretion regulation factor consisting of an amino acid sequence represented by SEQ ID NO: 2 or an amino acid sequence represented by SEQ ID NO: 4 had an activity of binding to arginine (see Working Example 1). Furthermore, not only the insulin secretion regulation factor of the present invention has a property of binding to arginine and insulin, but arginine and insulin competitively inhibit it (see Comparative Example 1). Thus, in the insulin secretion mechanism via the insulin secretion regulation factor of the present invention, as shown in FIG. 1, it is believed that when arginine is added, insulin bound to insulin secretion regulation factor localized in the endoplasmic reticulum migrates to the Golgi apparatus and to the secreting small vesicles, and then extracellularly secreted. Some of the polypeptides having the whole amino acid sequence that is included in the amino acid sequence represented by SEQ ID NO: 2 but has no amino acid sequence of SEQ ID NO: 4 (i.e. amino acid residues 1-1255 of SEQ ID NO: 2) or fragments thereof may function as an insulin secretion regulation factor of the present invention (data not shown).

It is well known that some of naturally occurring proteins or polypeptides include mutated proteins or polypeptides having therein one or several amino acid mutations derived from difference in the species of organism producing them or from the presence of gene mutation due to difference in the ectotype. Thus, the insulin secretion regulation factor of the present invention may have an amino acid sequence in which one or several amino acids have been deleted, substituted or added in an amino acid sequence represented by SEQ ID NO: 2 or SEQ ID NO: 4 as long as it has the above function.

The insulin secretion regulation factor of the present invention typically consisting of an amino acid sequence represented by SEQ ID NO: 2 or SEQ ID NO: 4 based on an analogy from the base sequence of the gene. However, it is not limited only to the protein having the sequence, and intended to include all homologous proteins as long as they have the characteristics described herein. There can be one to a plurality of amino acid mutations, preferably 1-20, more preferably 1-10, and method pfy 1-5 amino acid mutations.

It may have an identity of 70% or more, preferably 80% or more, more preferably 90% or more, and most preferably 98% with a protein having an amino acid sequence represented by SEQ ID NO: 2 or SEQ ID NO: 4.

The identity percentage may be determined by visual inspection or mathematical calculation. Alternatively, the identity percentage between two protein sequences may be determined based on the algorithm of Needleman, S. B. and Wunsch, C. D. (J. Mol. Biol. 48: 443-453, 1970) and by comparing the sequence information using the GAP computer program available from the University of Wisconsin Genetics Computer Group (UWGCG). Default parameters preferred for the GAP program may include: (1) the scoring matrix blosum62 as described in Henikoff, S, and Henikoff, J.

G. (Proc. Natl. Acad. Sci. U.S.A. 89:10915-10919, 1992); (2) a gap weight of 12; (3) a gap length weight of 4; and (4) no end gap penalty.

Other programs for sequence comparison to be used by a person skilled in the art may also be used. The identity percentage can be determined by comparing sequence information using a BLAST program described in, for example, Altschul, et al. (Nucl. Acids Res. 25, pp. 3389-3402, 1997). This program is available for the web site of the National Center for Biotechnology Information (NCBI) or the DNA Data Bank of Japan (DDBJ). Various conditions (parameters) for homology search with the BLAST program are described in detail in the above site, and search may usually be carried out using default values although some settings may be altered as appropriate.

Generally, when an amino acid was replaced with another amino acid having a similar property (for example, replacement of a hydrophobic amino acid to another hydrophobic amino acid, replacement of a hydrophilic amino acid to another hydrophilic amino acid, replacement of an acidic amino acid to another acidic amino acid, or replacement of a basic amino acid to another basic amino acid), the mutated protein obtained has a property similar to that of the original protein in most cases. The method of generating recombinant protein having the desired mutation using the gene recombinant technology is known to a person skilled in the art, and such a mutated protein is also included in the scope of the present invention.

(1-2) Method for Preparing the Insulin Secretion Regulation Factor of the Present Invention The expression, isolation and purification of the insulin secretion regulation factor of the present invention may be carried out using a known technology (for example, AME-immobilized magnetic nanobeads mentioned above). For example, the following method may be applied in a non-limiting manner.

The insulin secretion regulation factor of the present invention is (i) a protein comprising an amino acid sequence represented by SEQ ID NO: 2 or SEQ ID NO: 4; or (ii) a protein comprising an amino acid sequence in which one or several amino acids are deleted, substituted or added in an amino acid sequence represented by SEQ ID NO: 2 or SEQ ID NO: 4 and negatively regulating insulin secretion. The amino acid sequence (amino acid residues 1-1551) of SEQ ID NO: 2 and a protein-coding region (CDS) (nucleotides 176-4831) are published as NM_198899 in GenBank.

In brief, cDNA encoding insulin secretion regulation factor can be isolated from the cDNA library of insulin-secreting cells. Furthermore, by generating various primers for a polymerase chain reaction (PCR) and conducting PCR using combinations of primers with the cDNA clone of the insulin-secreting cells as the template, expression plasmids encoding various insulin secretion regulation factors (for example, a protein consisting of an amino acid sequence represented by SEQ ID NO: 2 or SEQ ID NO: 4) can be generated. As used herein, antisense primers of PCR primers can include a stop codon (TGA) and an ensuing restriction enzyme site.

cDNA obtained encoding insulin secretion regulation factor may be mutated using a known method such as described in Sambrook, J., et al., Molecular Cloning, A Laboratory Manual (3rd edition), Cold Spring Harbor Laboratory, 2001. Also, when one or a plurality of specific amino acids in an amino acid sequence represented by SEQ ID NO: 2 or 4 are to be replaced, a known point mutation method (Mullis, K. B., In Les Prix Nobel (ed. T. Frangsmyr), p. 107. Almqvist and Wilsell International, Stockholm, 1993; Smith, M., In Les Prix Nobel (ed. T. Frangsmyr), p. 123. Almqvist and Wilsell International, Stockholm, 1993) may be used.

As described above, the amino acid sequence and the base sequence of the insulin secretion regulation factor for use in the composition of the present invention are the amino acid sequence of SEQ ID NO: 2 and the base sequence of SEQ ID NO: 1, which are the amino acid sequence of a known mouse glycosyltransferase and the base sequence encoding it. Using these known sequences or part thereof, genes encoding protein having a similar physiological activity can be easily isolated from other biological species by genetic engineering technology such as nucleic acid amplification reaction, e.g. PCR. In such cases, those genes and proteins or polypeptides encoded thereby can also be used in order to obtain an insulin secretion regulation factor having an amino acid sequence in which one or several amino acids are deleted, substituted or added in an amino acid sequence in the amino acid sequence of the insulin secretion regulation factor of the present invention.

The hybridization condition to be used in screening of homologous genes is not specifically limited, but preferably it is generally a stringent condition such as 6×SSC, 5×Denhardt's, 0.1% SDS and 25° C.-68° C. In this case, as the hybridization temperature, more preferably 45° C.-68° C. (without formamide) or 25° C.-50° C. (50% formamide) may be mentioned. It is well known to a person skilled in the art that DNA comprising the base sequence having a homology greater than a given homology can be cloned by setting, as appropriate, the hybridization condition such as formamide concentration, salt concentration and temperature, and homologous genes thus cloned are all included in the scope of the present invention.

The nucleic acid amplification reaction comprises, for example, reactions that requires temperature cycle such as the polymerase chain reaction (PCR) (Saiki, R. K., et al., Science 230:1350-1354, 1985), the ligase chain reaction (LCR) (Wu, D. Y. and Wallace, R. B., Genomics 4:560-569, 1989; Barringer, K. J., Gene 89:117-122, 1990; Barany, F., Proc. Natl. Acad. Sci. U.S.A. 88:189-193, 1991), and transcription-based amplification (Kwoh, D. Y., et al., Proc. Natl. Acad. Sci. U.S.A. 86:1173-1177, 1989), as well as constant-temperature reactions such as the strand displacement amplification (SDA) (Walker, G. T., et al., Proc. Natl. Acad. Sci. U.S.A. 89:392-396, 1992; Walker, G. T., et al., Nucl. Acids Res. 20:1691-1696, 1992), self-sustained sequence replication (3SR) (Guatelli, J C, 1990, Proc. Natl. Acad. Sci. U.S.A. 87, p. 1874-1878), and Qβ replicase system (Lizardi, et al., Biotechnology, 6: 1197-1202, 1988). Also, amplification based on nucleic acid sequence by competitive amplification of a target nucleic acid and a mutated sequence (Nucleic Acid Sequence Based Amplification: NASABA) described in EPA No. 0525882 can also be used. Preferably it may be a PCR method.

Homologous genes cloned using the hybridization, nucleic acid amplification reaction, etc., as described above may preferably have an at least 70% or more, preferably 80% or more, more preferably 90% or more, still more preferably 95% or more, and most preferably 98% or more of homology with the base sequence represented by SEQ ID NO: 1 or 3.

The identity percentage may be determined by visual inspection or mathematical calculation. Alternatively, the identity percentage between two nucleic acid sequences may be determined by comparing sequence information using a GAP computer program, version 6.0, described in Devereux, et al., (Nucl. Acids Res., 12:387 (1984)) and available from the University of Wisconsin Genetics Computer Group (UWGCG). Default parameters preferred for the GAP program may include: (1) the single (unary) comparison matrix on nucleotide (having the value of 1 for identity and 0 for non-identity), and the weighted comparison matrix of Gribskov and Burgess, Nucl. Acids Res., 14:6745 (1986) as described in Schwartz and Dayhoff ed., Atlas of Protein Sequence and Structure, National Biomedical Research Foundation, pp. 353-358 (1979); (2) a penalty of 0.3 to each gap and a further penalty of 0.10 to each sign in each gap; and (3) no end gap penalty. Other programs for sequence comparison used by a person skilled in the art can also be used.

The desired insulin secretion regulation factor can be obtained in large quantities using genetic engineering by introducing a nucleic acid obtained encoding insulin secretion regulation factor into *Escherichia coli*, yeast or insect cells using recombinant vectors multiplicable in respective hosts and then allowing them to be expressed.

Cloning vectors and expression vectors suitable for use in the hosts of bacteria, fungi, yeast, and mammal cells are described in, for example, Pouwels, P. H., et al., Cloning Vector; A Laboratory Manual, Elsevier, NY, 1986. The expressed insulin secretion regulation factor can be purified by, but not limited to, combination of a arginine interacting factor-purifying column chromatography, molecular sieve chromatography, gelatin column chromatography, and immunoaffinity chromatography. The purified insulin secretion regulation factor can be analyzed by the silver staining method and the Western blotting method using anti-insulin secretion regulation factor antibody.

More specifically, according to the present invention, a recombinant vector for integrating a gene to be used in protein expression can be generated using a known method. As a method for integrating a DNA fragment of the insulin secretion regulation factor of the present invention into a vector such as plasmid, there can be mentioned a method described Sambrook, J., et al., Molecular Cloning: A Laboratory Manual (3rd edition), Cold Spring Harbor Laboratory, 1, 1 (2001), and the like. Conveniently, a commercially available ligation kit (such as the one manufactured by Takara Shuzo) can be used. A recombinant vector (for example, a recombinant plasmid) thus obtained can be introduced into host cells (for example, *E. coli* TB1, LE392, XL-1Blue, etc.).

A person skilled in the art can also select, as appropriate, restriction ends so as to be adapted to a recombinant vector, and furthermore a recombinant vector suitable for host cells can be selected as appropriate so as to allow the expression of the desired protein. Preferably, such a vector may have been or may be constructed in such a way that regions (as needed, a point of autonomous replication, a conjugal transfer region, a selection marker such as kanamycin resistant gene, etc.) that function to cause homologous recombination between the gene for use in the present invention and the gene of interest on the host cell have been appropriately arranged or are introduced, so that said nucleic acids are appropriately recombined.

With regard to the purpose of producing the desired protein, an expression vector is specifically useful. The type of expression vector may not be specifically limited as long as it can express the desired gene in various host cells such as procaryotic cells and/or eucaryotic cells. For example, as an expression vector for *E. coli*, pGEX, pQE-30, pQE-60, pMAL-c2, pMAL-p2, pSE420, etc., may be preferred, as an expression vector for yeast, pYES2 (*Saccharomyces* spp.), pPIC3.5K, pPIC9K, pAO815 (these are *Pichia* spp.), etc., may be preferred, and as an expression vector for insects, pBacPAK8/9, pBK283, pVL1392, pBlueBac4.5, etc., may be preferred.

An example of expression vector for expression in mammals is a vector construct as described by Okayama and Berg (Mol. Cell. Biol., 3:280, 1983). A system useful for the stable and high level expression of mammal cDNA in c127 mouse mammary gland epithelial cells may be constructed as substantially reported by Cosman, et al. (Mol. Immunol., 23:935, 1986). Alternatively, as a vector for expression in neural cells, in vivo or in vitro, for example an adenovirus vector or a modified vector (PEF-CITE-neo: Miyata, S., et al., Clin. Exp. Metastasis, 16:613-622, 1998) of pEF-BOS vector (Mizushima, S., et al., Nucl. Acids Res., 18: p. 5322, 1990) can be used.

A transformant can be prepared by introducing the desired expression vector into a host cell. The host cell to be used may not be specifically limited as long as it is consistent with the expression vector and can be transformed. In the technical field to which the present invention pertains, a variety of cells such as commonly used natural cells, or artificially established recombinant cells can be used. There can be illustrated, for example, bacteria (*Escherichia* spp., *Bacillus* spp.), yeast (*Saccharomyces* spp., *Pichia* spp.), animal cells, insect cells, plant cells and the like. Specifically, there can be mentioned *E. coli* (M15, JM109, BL21, etc.), yeast (INVSc1 (*Saccharomyces* spp.), GS115, KM71 (these are *Pichia* spp.), etc.), insect cells (BmN4, silkworm larvae, etc.), and the like. As animal cells there can be mentioned cells derived from mouse, *Xenopus laevis*, rat, hamster, monkey, or human, or cultured cell lines established from these cells.

When a bacteria such as *E. coli* in particular is used as the host cell, an expression vector may generally be composed of a promoter/operator region, a start codon, a gene encoding the desired antimicrobial protein, a stop codon, a terminator, and a replication-competent unit.

When a yeast, a plant cell, an animal cell or an insect cell is used as the host cell, an expression vector may generally be composed of a promoter, a star codon, a gene encoding the desired antimicrobial protein, a stop codon, and a terminator. It may also contain DNA encoding a signal peptide, an enhancer sequence, a 5'-end or 3'-end untranslated region of the desired gene, a selection marker region or a replication-competent unit as appropriate.

As a start codon for the vector of the present invention, a methionine codon (ATG) may be illustrated. As a stop codon, a conventionally used stop codon (for example, TAG, TGA, TAA, etc.) may be illustrated.

The replication-competent unit means DNA having an ability of replicating the entire DNA sequence in a host cell, and includes a naturally occurring plasmid, an artificially modified plasmid (plasmid prepared from a naturally occurring plasmid), a synthetic plasmid and the like. As a suitable plasmid, there can be mentioned plasmid pQE30, pET or pCAL or artificial modifications thereof (DNA fragments obtained by treating pQE30, pET or pCAL with an appropriate restriction enzyme) for *E. coli*, plasmid pYES2 or pPIC9K for yeast, plasmid pBacPAK8/9 for insect cells, and the like.

As an enhancer sequence and a terminator sequence, those commonly used by a person skilled in the art such as those derived from SV40, etc., can be used.

As a selection marker, a commonly used one can be used in a conventional method. There can be mentioned a gene resistant to antibiotics such as tetracycline, ampicillin, or kanamycin or neomycin, hygromycin or spectinomycin.

An expression vector can be prepared by conjugating, at least, the above promoter, a start codon, a gene encoding the desired antimicrobial protein, a stop codon, and a terminator region in a sequential or circular manner to a suitable replication-competent unit. At this time, an appropriate DNA fragment (for example, a linker, another restriction site, etc.) can be used by a conventional method such as digestion with a restriction enzyme and ligation with T4 DNA ligase.

The introduction of the above expression vector into the host cell can be carried out using a conventionally known method. For example, for bacteria (*E. coli, Bacillus subtilis*, etc.), for example, Cohen's method (Proc. Natl. Acad. Sci. U.S.A., 69:2110, 1972), a protoplast method (Mol. Gen. Genet., 168:111, 1979) and a competent method (J. Mol. Biol., 56:209, 1971), for *Saccharomyces cereviceae*, for example, Hinnen et al.'s method (Proc. Natl. Acad. Sci. U.S.A., 75:1927, 1978) and a lithium method (J. Bacterial., 153:163, 1983), for plant cells, a leaf disk method (Science, 227:129, 1985) and an electroporation method (Nature, 319: 791, 1986), for animal cells, for example, Graham's method (Virology, 52:456, 1973), for insect cells, for example, Summers et al.'s method (Mol. Cell. Biol., 3:2156-2165, 1983) can be used for respective transformations.

The purification and isolation of the protein or polypeptide of the present invention can be carried out by combining, as appropriate, methods commonly used for the purification and isolation of proteins such as an arginine interacting factor-purifying column chromatography, an ammonium sulfate precipitation method, and an ion exchange chromatography (Mono Q, Q Sepharose or DEAE, etc.). For example, in a case where an insulin secretion regulation factor is accumulated in host cells, the host cells are collected by a procedure such as centrifuge and filtration, and after suspending the collected cells in a suitable buffer solution (for example, a buffer solution such as about 10-100 mM Tris buffer, phosphate buffer, HEPES buffer and MES buffer; pH may differ with the buffer used, but may preferably be in the range of pH 5.0-9.0), the cells are disrupted with a method suitable for the host cells used, and centrifuged to obtain the contents of the host cell. On the other hand, in a case where the insulin secretion regulation factor is extracellularly secreted, the host cells and the culture medium are separated by a procedure such as centrifuge and filtration to obtain a culture filtrate. After disrupting the host cells, or using the culture filtrate as it is, or carrying out ammonium sulfate precipitation and dialysis, protein can be subjected to purification and isolation. As the methods of purification and isolation, the following can be mentioned. Thus, when the protein is to be tagged with a tag such as 6×histidine, GST, or maltose-binding protein, a commonly used affinity chromatography-based method suitable for each tagging can be mentioned. On the other hand, in a case where protein is produced without such tagging, a method based on affinity chromatography using antibody can be used. Also, in addition to this, combination of ion exchange chromatography, gel filtration and hydrophobic chromatography, isoelectric focusing chromatography, etc., can be mentioned.

For protein labelling, a fluorescent dye, in addition to the above, can be introduced to a protein. For example, after preparation of a protein, a fluorescent molecule may be added to the protein by a chemical labelling method that targets a specific group in the protein (a protein having a specific amino acid sequence may be prepared by gene recombinant technology, and based on the characteristics of the amino acid sequence, a fluorescent dye can be added). As a fluorescent dye, any fluorescent dye commonly used in the technical field to which the present invention pertains, such as TAMRA (carboxymethyl rhodamine), TMR (tetramethyl rhodamine), Alexa 647, Rhodamine Green, Alexa 488 can be used. Alternatively, a fluorescence-emitting protein (GFP fusion protein, etc.) may be prepared using gene recombinant technology.

(1-3) A Composition Comprising the Insulin Secretion Regulation Factor of the Present Invention According to the present invention, an insulin secretion regulating composition comprising insulin secretion regulation factor is provided. Since the insulin secretion regulation factor negatively regulates insulin secretion, the composition of the present invention can be used in vivo, in vitro, or ex vivo in screening of an antidiabetic drug described below. In another embodiment, a kit for controlling insulin secretion containing the composition of the present invention can be used. The kit may include, as desired, a suitable container, a manufacturer's instruction, etc.

According to the present invention, a composition comprising insulin secretion regulation factor is also useful as a pharmaceutical composition. The composition of the present invention can also be used in the maintenance and treatment of insulin secretion ability of pancreatic β cells. In this regard, it also be used in the treatment or prevention of diabetes mellitus derived from abnormal pancreatic β cells. When diabetes mellitus is to be treated or prevented, the pharmaceutical composition of the present invention comprises a therapeutically effective amount of insulin secretion regulation factor in a mixture with a carrier acceptable as a pharmaceutical drug. The composition of the present invention may be administered systemically or locally, preferably parenterally such as intravenously, subcutaneously, and intramuscularly.

The dosage and administration of the composition of the present invention can be determined by an attending physician considering the effect of the drug, for example the nature and/or severity of the symptoms of the patient, body weight, sex, diet, administration timing, as well as various factors such influencing other clinical conditions. A person skilled in the art can determine the dosage of the composition of the present invention based on these elements.

The insulin secretion ability at the target site can be regulated by preparing an expression vector having integrated therein a gene encoding insulin secretion regulation factor, and allowing it to be expressed in vivo at the target site (for example the pancreas) or transferring the cell having integrated therein said expression vector to the target site (for example the pancreas).

2. Screening Method of an Antidiabetic Drug Using the Insulin Secretion Regulation Factor of the Present Invention (2-1) A Screening Method Based on the Binding Activity to Insulin Secretion Regulation Factor According to the present invention, there is provided a screening method which comprises selecting a test substance having an activity of binding to insulin secretion regulation factor, based on the activity of the test substance to bind to the insulin secretion regulation factor, as a candidate substance for use in a drug for treating or preventing diabetes mellitus, said method comprising the steps of: (a) preparing the insulin secretion regulation factor of the present invention; (b) bringing the test substance into contact with the protein prepared in step (a); and (c) selecting the test substance that bound to said protein as a candidate substance for use in a drug for treating or preventing diabetes mellitus.

By using the insulin secretion regulation factor of the present invention, a substance that binds to the insulin secretion regulation factor thereby to promote insulin secretion can be screened. Since arginine and insulin competitively bind to the insulin secretion regulation factor of the present invention to regulate insulin secretion as described above, the substance that bound to the insulin secretion regulation factor of the present invention is also a substance having a possibility of promoting at least insulin secretion similarly to arginine.

Thus, the insulin secretion regulation factor of the present invention having such characteristics can screen a candidate substance that could be an active ingredient of an antidiabetic drug (specifically, an insulin secretion-promoting drug). The arginine-binding ability of the insulin secretion regulation factor of the present invention has been described in detail in Working Example 1 described below.

As a test substance to be subjected to the screening of the present invention, there can be used, but not limited to, known compounds (including peptides) that have been registered in chemical files, compound groups obtained by the combinatorial chemistry technology (Terrett, N. K., et al., Tetrahedron, 51:8135-8137 (1995)), or random peptide groups generated using the phage display method (Felici, F., et al., J. Mol. Biol., 222:301-310 (1991)). Also, culture supernatants or homogenates of cells or microorganisms, naturally occurring ingredients derived from plants or marine organisms, or extracts from animal tissues can also be used as a test substance for screening. Since the present invention intends to screen a drug for diabetes mellitus associated with abnormal insulin secretion, the test substance selected by the screening method of the present invention or a candidate substance may have either an insulin secretion-promoting activity or insulin secretion-inhibiting activity.

(2-2) A Screening Method Using Cells in which Insulin Secretion Regulation Factor was Forcibly Expressed According to the present invention, there is provided a screening method which comprises selecting a test substance having an activity of promoting insulin secretion, based on said insulin secretion-promoting activity of the test substance, as a candidate substance for use in a drug for treating or preventing diabetes mellitus, said method comprising the steps of:

(a) preparing transformed cells that were transformed or homologously recombined on the chromosome with a recombinant vector having integrated therein the following nucleic acid:

(i) a nucleic acid comprising the base sequence represented by SEQ ID NO: 1 or SEQ ID NO: 3; or (ii) a nucleic acid hybridizing under a stringent condition to a nucleic acid that comprises the base sequence represented by SEQ ID NO: 1 or SEQ ID NO: 3 and encoding a protein that negatively regulates insulin secretion;

(b) bringing the test substance into contact with the transformed cells prepared in step (a) and the untransformed control cells;

(c) determining the amount of insulin secreted in said respective cells; and (d) selecting a test substance that restores the insulin secretion of said transformed cells relative to said control cells as a candidate substance for use in a drug for treating or preventing diabetes mellitus. In one embodiment, the nucleic acid in the above step (a) is (i) a nucleic acid consisting of the base sequence represented by SEQ ID NO: 1 or SEQ ID NO: 3; or (ii) a nucleic acid hybridizing under a stringent condition to a nucleic acid that consists of the base sequence represented by SEQ ID NO: 1 or SEQ ID NO: 3 and encoding a protein that negatively regulates insulin secretion.

Figure 4:
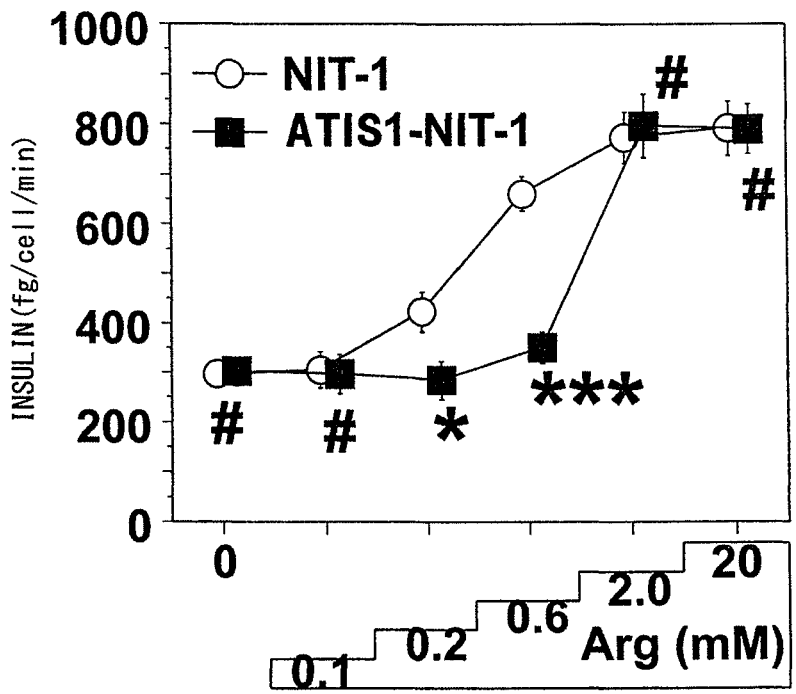
FIG. 4 shows the result of regulation of arginine-induced insulin secretion in NIT-1 cells in which insulin secretion regulation factor was forcibly expressed.

By using a newly found characteristics that in a cultured cell having introduced therein an insulin secretion regulation factor, insulin secretion is negatively regulated, the screening method of the present invention comprises selecting a test substance that releases such negative regulation, i.e. restores the insulin secretion of the cultured cell, as a candidate drug for an insulin secretion-promoting drug. As described in the Working Example 2 described below, in the comparison of the cultured cells in which the insulin secretion regulation factor of the present invention was forcibly expressed and the wild type control cells in which there was no such forced expression, the amount of insulin secreted increases as the concentration of arginine (insulin secretion-promoting substance) increases in the control cells having no forced expression (FIG. 4). On the other hand, in the cultured cells for which forced expression was conducted, insulin secretion was not promoted up to 0.6 mM of arginine at most ("negative regulation"), and the insulin secreting ability comparable to the control cell was restored at a concentration of 2.0 mM (FIG. 4). Thus, by using the cultured cells in which the insulin secretion regulation factor of the present invention was forcibly expressed, an insulin secretion-promoting substance (for example, purified naturally occurring drupanin (Dru), purified naturally occurring baccharin (Bac), chemically synthesized baccharin (sBac), UDP-glucose) such as arginine can be selected (see Working Examples 4 and 6 described below).

As used herein the term "negative regulation" indicates a state in which in the cells having introduced therein the insulin-regulating gene of the present invention, the insulin secretion ability by an insulin secretion-promoting substance is decreased relative to the control cells having introduced therein no such gene. Also, "restoring" of the insulin secreting ability by an insulin secretion-promoting substance indicates that the amount of insulin secreted of the transformed cells approaches that of the control cells in the comparison of the amount of insulin secreted by the same concentration of insulin secretion-promoting substance added. The restoring of the insulin secretion ability of the transformed cells by an insulin secretion-promoting substance may be 5% or more, preferably 10% or more, more preferably 20% or more, still more preferably 30% or more, further preferably 50% or more, still more preferably 75% or more, and most preferably 100%. The amount of insulin secreted by the cells can be determined using a method known in this field (for example, Nomura, et al., Bioorg. Med. Chem., 11:3807-3813 (2003)), or a commercially available kit (for example, Shibayagi Co., Ltd., Levis insulin measurement ELISA kit).

According to the present invention, there are provided transformed cells for use in screening an antidiabetic drug. The transformed cells of the present invention may be any cells that have the above characteristics, and their preparation method or other characteristics are not specifically limited. More typically, they are cells that were transformed or homologously recombined with a recombinant vector having integrated therein (i) a nucleic acid consisting of the base sequence represented by SEQ ID NO: 1 or SEQ ID NO: 3; or (ii) a nucleic acid hybridizing under a stringent condition to a nucleic acid that consists of the base sequence represented by SEQ ID NO: 1 or SEQ ID NO: 3 and encoding a protein that negatively regulates insulin secretion. The transformed cells of the present invention can be obtained by integrating the above isolated nucleic acid into an appropriate vector, and transforming the vector into the host cell (preferably eucaryotic cells, preferably NIT-1 cells). By introducing a suitable promoter and a sequence involved in trait expression into these vectors, the insulin secretion-promoting substance can be expressed in the respective host cells. The method of culturing transformed cells for use in the screening method of the present invention may be carried out according to a method commonly used in the culturing of host cells. However, in order to accurately determine the insulin secretion-promoting activity of a test substance, it may not be preferred to include an insulin secretion-promoting substance such as arginine in the medium used. Thus, except in an experiment for determining the effect of arginine addition on insulin secretion, it may be preferred to use an arginine-free medium.

(2-3) Screening Method Using an Animal in which Insulin Secretion Regulation Factor was Forcibly Expressed According to the present invention, there is provided a screening method which comprises selecting a test substance having an activity of promoting insulin secretion, based on said insulin secretion-promoting activity of the test substance, as a candidate substance for use in a drug for treating or preventing diabetes mellitus, said method comprising the steps of:

(a) preparing a transgenic animal other than a human which contains or homologously recombined on the chromosome with a recombinant vector having integrated therein the following nucleic acid:
(i) a nucleic acid comprising the base sequence represented by SEQ ID NO: 1 or SEQ ID NO: 3; or
(ii) a nucleic acid hybridizing under a stringent condition to a nucleic acid that comprises the base sequence represented by SEQ ID NO: 1 or SEQ ID NO: 3 and encoding a protein that negatively regulates insulin secretion;

(b) administering the test substance to the transgenic animal prepared in step (a) or a control animal having no nucleic acid mentioned above;

(c) determining blood insulin concentration in said respective animals; and (d) selecting a test substance that restores the insulin secretion of said transformed cells relative to said control cells as a candidate substance for use in a drug for treating or preventing diabetes mellitus. In one embodiment, the nucleic acid in the above step (a) is (i) a nucleic acid consisting of the base sequence represented by SEQ ID NO: 1 or SEQ ID NO: 3; or (ii) a nucleic acid hybridizing under a stringent condition to a nucleic acid that consists of the base sequence represented by SEQ ID NO: 1 or SEQ ID NO: 3 and encoding a protein that negatively regulates insulin secretion.

Figure 5:
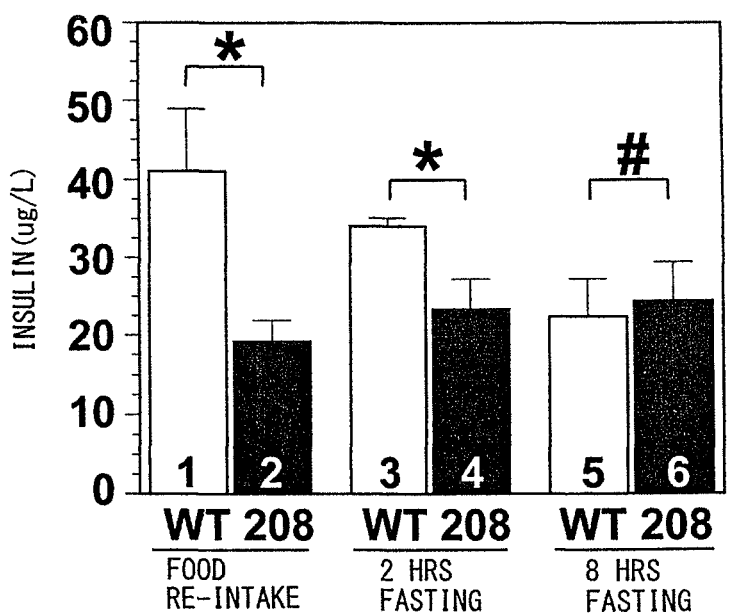
FIG. 5 shows insulin secretion in a mouse (208) in which insulin secretion regulation factor was forcibly expressed.

The screening method of the present invention comprises using a newly found characteristics that insulin secretion is negatively regulated in a transgenic animal having introduced therein an insulin secretion regulation factor in order to select a test substance that releases such negative regulation, i.e. restores the insulin secretion of the transgenic animal, as a candidate drug for an insulin secretion-promoting drug. As described in Working Example 3 described below, the present inventors have succeeded in generating transgenic mice in which insulin secretion regulation factor has been forcibly expressed in a pancreatic β cell-specific manner. In the comparison of the transgenic mice of the present invention and non-transgenic control mice, the amount of insulin secreted was high in the control mice after food intake, whereas it was low in the transgenic mice ("negative regulation"). Then, in the measurement of the amount of insulin secreted with time, the amount of insulin secreted decreased in the control mice, and after fasting for 8 hours, little difference was noted in the amount of insulin secreted between the transgenic mice and the control mice (FIG. 5). Thus, by using a transgenic animal in which the insulin secretion regulation factor of the present invention was forcibly expressed, an insulin secretion-promoting substance such as arginine can be selected.

As used herein the terms "negative regulation" and "restoring" are as defined with regard to the cells having introduced therein the insulin-regulating gene of the present invention. In the control animal, generally blood insulin concentration is high after food intake, and as fasting continues, the concentration decreases with time, and thus the restoring of blood insulin concentration in the transgenic animal naturally includes cases where the transgenic animal and the control animal come to show no difference in blood insulin concentration any more at a certain period of time after fasting. The certain period of time may differ with the amount of food intake by the animal and the type of the animal, but may usually be 1-24 hours, preferably 2-8 hours, and more preferably 8 hours. Blood insulin concentration in the animal can be determined using a method known in this field (for example, the aggregation method, the immune reaction method), or a commercially available kit (for example, Shibayagi Co., Ltd., Levis insulin measurement ELISA kit).

According to the present invention, there are provided transgenic animals other than human for use in screening antidiabetic drugs. The non-human transgenic animal of the present invention may be any animal that has the above characteristics, and the method of preparation thereof or other characteristics are not specifically limited. More typically, they are animals other than human that were transformed or homologously recombined on the chromosome with a recombinant vector having integrated therein (i) a nucleic acid consisting of the base sequence represented by SEQ ID NO: 1 or SEQ ID NO: 3; or (ii) a nucleic acid hybridizing under a stringent condition to a nucleic acid that consists of the base sequence represented by SEQ ID NO: 1 or SEQ ID NO: 3 and encoding a protein that negatively regulates insulin secretion. In order to attain the object of the present invention, i.e. to screen an antidiabetic drug, as the cells into which the above nucleic acid is intended to be introduced, pancreatic β cells, without limitation, can be targeted. Said cells comprises a promoter that specifically functions in said cells and the above nucleic acid (gene) under the control of this promoter, and said gene has been expressively introduced. In the screening of the present invention, it is possible to generate not only a transgenic animal having a gene encoding insulin secretion regulation factor, but also a transgenic animal that further comprises one or more gene capable of altering insulin secretion for a diabetic model (for example, a double transgenic animal, a triple transgenic animal). As the gene associated with diabetes mellitus, in addition to a gene encoding the insulin secretion regulation factor of the present invention, there can be mentioned, for example, gene encoding adiponectin, resistin, and PPARγ associated with insulin resistance, and gene encoding Kir6.2, amilin, HNF-4α associated with insulin secretion disorder. Also, a double transgenic animal can also be obtained by crossing a transgenic animal in which one of the two genes to be introduced has been introduced and a transgenic animal in which the other gene has been introduced.

Animals other than human (non-human animals) are, for example, vertebrates, and may preferably be mammals. As mammals, for example, mice, rats, guinea pigs, hamsters, rabbits, goats, pigs, dogs, and cats may be mentioned. Preferably they may be mice and rats. Transgenic animals other than human of the present invention should be understood in a broad sense to include not only the individual non-human animal, but part of the non-human animal such as the cells, tissues, organs, etc., of the non-human animal.

As used herein, a specific gene is called an endogenous gene when it is localized at the original position on the chromosome of a non-human animal, and is called an exogenous gene (or introduced gene) when it is localized at a position different from the original position on the chromosome. In the transgenic animal of the present invention other than human, a gene in which a promoter that specifically functions in the pancreatic β cells and a gene encoding a protein under the control of the promoter have been conjugated (hereinafter referred to as "conjugated gene") may preferably be an exogenous gene.

According to the present invention, the promoter that specifically functions in the pancreatic β cells of the above animal may be, but not limited to, any transcription regulatory region of a gene specifically expressed in the pancreatic β cells. A preferred example of a promoter that specifically functions in the pancreatic β cells is an insulin promoter. Also, as a promoter that functions in the pancreatic β cells, cytomegalovirus (CMV) promoter, CMV enhancer+actin promoter, EF-1 promoter may be mentioned. The transgenic animal other than human of the present invention may preferably be a transgenic animal other than human obtained by transformation of a gene constructed by conjugating an insulin promoter and a gene encoding an insulin secretion promotion factor. The species of the pancreatic β cells-specific promoter of the present invention may be not be limited, and humans, rats, mice, etc., can be used.

The conjugated gene constructed as above was used as an introduced gene, and introduced into germ cells of an animal other than human by the transgene method to generate transgenic animal cells. Then by developing the cells, a transgenic animal other than human can be generated. In the above "transgene method," a plurality of copies of the introduced gene are introduced at unspecified positions of genomic DNA carried by the host of the introduced gene. As used herein, a transgene method that employs a gene encoding an insulin promoter+an insulin secretion regulation factor as the introduced gene may preferably be used.

As used herein, the cell to be used as the host may be any non-human cell, and may not be specifically limited. For example, a fertilized egg other than human can be used. A method for introducing an introduced gene into a fertilized egg other than human will be explained in detail below. The fertilized egg other than human to be used herein may be any gene that expresses a gene encoding insulin secretion promotion factor by the activity of the promoter region by the introduction, development and growth of the introduced gene, and may not be specifically limited. Such a fertilized egg can be obtained by crossing a male and a female of an animal other than human. By injecting the introduced gene, by the microinjection method, into a fertilized egg obtained, and then artificially transferring and transplanting it into the oviduct of the female animal and allowing the animal to give birth, a transgenic animal can be obtained. As a fertilized egg of the mouse mentioned above, those obtained by crossing of mice derived from, for example, B6C3F1, C57BL/6, 129/sv, BALB/c, C3H, SJL/Wt, etc., can be used.

The amount of the introduced gene may suitably be 100-3,000 copies. As the method for introducing the introduced gene, commonly used methods such as the microinjection method and electroporation method can be mentioned. As used herein, the baby mouse into which the above introduced gene has been introduced can be selected by excising the tail tip of the mouse, extracting genomic DNA using the polymer DNA extraction method (HASSEI KOUGAKU JIKKENN (Developmental Engineering Experiment) Manual, edited by Tatsuji Nomura and Motoya Katsuki, Kodansha Ltd. (1987)) or a commercially available kit such as the DNAeasy Tissue Kit (manufactured by QIAGEN), and confirming the presence of a gene encoding insulin secretion promotion factor using a commonly used method such as the Southern blotting method and the PCR method. Furthermore, the actual expression of the introduced gene encoding insulin secretion promotion factor in the individual and the production of insulin secretion promotion factor can be confirmed by a commonly used method such as the Northern blotting method and Western blotting method. Also by introducing a gene so as to express a fusion protein of a fluorescent protein (for example GFP) and insulin secretion promotion factor, the expression of insulin secretion promotion factor can be visualized in vivo. Part of the non-human animal generated such as the cells, tissues, organs, etc., of the non-human animal are also within the scope of the present invention.

For example, by administering a test substance to a transgenic animal other than human of the present invention, and observing changes in the amount of the insulin secretion promoting factor in the pancreatic β cells and in its localization due to this administration, the functional or morphological changes in the pancreatic β cells in response to the above administration can be analyzed. Based on such an analysis, the insulin secretion ability induced by the administration of a test substance to the pancreatic β cells can be elucidated. The findings obtained from these analyses can lead to the elucidation of pharmacological mechanism on diabetic disorders associated with pancreatic β cells. As a method for treating a transgenic animal with a test substance, a commonly used method such as oral administration, intravenous injection, and co-culturing can be used. They may be selected as appropriate depending on the condition (individual, cells, tissues, organs, etc.) of the transgenic animal, the property of the test substance and the like. The amount of the test substance to be treated can also be selected as appropriate depending on the treatment method, the property of the test substance and the like.

(2-4) A Screening Method Using a Knock-Out Animal for Insulin Secretion Regulation Factor According to the present invention, there is provided a screening method which comprises selecting a test substance having an activity of inhibiting insulin secretion, based on its insulin secretion-inhibiting activity, as a candidate substance for use in a drug for treating or preventing diabetes mellitus, said method comprising the steps of:

(a) preparing a knock-out animal other than human in which the expression of a gene for the following protein has been partially or completely inhibited:

(i) a protein comprising an amino acid sequence represented by SEQ ID NO: 2 or SEQ ID NO: 4; or (ii) a protein comprising an amino acid sequence in which one or several amino acids are deleted, substituted or added in an amino acid sequence represented by SEQ ID NO: 2 or SEQ ID NO: 4 and negatively regulating insulin secretion;

(b) administering the test substance to the knock-out animal prepared in step (a) and a control animal in which the above gene expression has not been inhibited;

(c) determining blood insulin concentration in each of the above animals; and (d) selecting a test substance that restores the insulin secretion of said knock-out animal to normal relative to said control animal as a candidate substance for use in a drug for treating or preventing diabetes mellitus.

The present invention uses a fact that in a knock-out animal other than human in which the expression of a gene for insulin secretion regulation factor has been partially or completely inhibited, insulin secretion by said factor is not negatively regulated and thus the animal is at a high insulin state, in order to select a test substance that inhibits insulin secretion as a candidate substance for an insulin secretion inhibiting drug. The present invention will become a useful tool for the development of a therapeutic agent that inhibits excessive insulin secretion due to abnormal pancreatic β cells such as hyperinsulinemic diabetes.

According to the present invention, a knock-out animal other than human for use in the screening method of the present invention is provided. In the knock-out animal other than human of the present invention, the gene expression of the above protein targeting the pancreatic β cells may preferably be partially or completely inhibited. As used herein the term "partially" indicates a state of gene expression in which the normal protein cannot be expressed or the expressed protein cannot play its original function due to deficiency of part of the base sequence encoding the above protein.

The knockout mouse of the gene for insulin secretion regulation factor may be a mouse that can be obtained by generating a knockout mouse by homologous recombination between a gene-deficient targeting vector and a mouse genome in an embryonic stem cell (ES cell) in a conventional method, and then back crossing with a wild type mouse such as a C57/BL/6 mouse. For example, a knockout mouse can be obtained according to the description in "Latest Technology of Gene Targeting" (Ken Yagi, ed., Yodosha, 2000), Gene Targeting (translation supervisor Tetsuo Noda, Medical Science International Ltd., 1995) and the like. Also, a knockout mouse can be generated by deleting the function of said gene by a "method for inhibiting gene expression" such as the knock-down of the gene by the small interfering RNA method (Brummelkamp, T. R., et al., Science, 296, 5501-553 (2002)). In the screening method of the present invention, not only an animal in which the expression of gene encoding insulin secretion regulation factor has been inhibited but also a knock-out animal (for example, a double knock-out animal, a triple knock-out animal) in which the expression of one or more genes that modify insulin secretion for diabetes mellitus model has been inhibited can be generated. For example, a double knock-out animal can be obtained as a heterozygous (+/−) double knock-out animal obtained by crossing a chimera animal obtained by crossing an animal in which one of the two genes to be knocked-out has been knocked-out and an animal in which the other gene has been knocked-out with a wild type animal, or as a homozygous (−/−) double knock-out animal obtained by further crossing heterozygous animals with each other.

Mammals for use as knock-out animals of the present invention may be any mammals for which the regenerating system from embryonic stem (ES) cells have been established, and there can be mentioned mammals selected from the group consisting of mice, rats, guinea pigs, hamsters, sheep, monkeys, goats, pigs, horses, cattle, monkeys, rabbits, dog and cat. Preferably they may be mice.

In the screening method of the present invention using a knock-out animal, the measurement of blood insulin concentration, the administration of a test substance, etc., may be carried out in the same manner as described in the case of the above transgenic animal.

The present invention will now be explained in further detail with reference to examples below, but it should be noted that the present invention is not limited to them in any way.

EXAMPLES

Working Example 1

Characterization of Insulin Secretion Regulation Factor (1) Isolation and Identification of Insulin Secretion Regulation Factor It is known that arginine plays a variety of roles in vivo, and among others it is involved in insulin secretion. However, as described above, little is known about an arginine interacting factor (AIF) that directly mediates the physiological effects of arginine. Using arginine methyl ester (AME)-immobilized magnetic nanobeads, the present inventors previously identified phosphofructokinase (PFK), RuvB-like 2 (RBL2), and RuvB-like 1 (RBL1) as AIF (Non-patent document 4) from the extract of HeLa cells, a non-insulin secreting cells (Non-patent document 4). As described in Non-patent document 4, while AME is a potent induction factor of insulin production similarly to arginine, AME is an antagonist of nitrogen oxide synthase (NOS) similarly to nitro-arginine-methyl (NAME). On the other hand, arginine is a substrate for NOS, and NOS produces NO from arginine. Since inducible NOS (iNOS) has been regulated on the level of transcription and translation, it does not respond for 15-30 minutes after stimulation, but arginine-induced promotion of insulin secretion takes place in as fast as 1-5 minutes. Thus, since the action mechanisms of AME and arginine on insulin secretion are different, the target of arginine was estimated to be a novel substance instead of NOS.

Thus, using AME-immobilized magnetic beads, the present inventors have isolated and purified insulin secretion regulation factor, and have found, from mass analysis and database search, that this factor has the same amino acid sequence as a certain glycosyltransferase registered to GenBank as NM__198899. Based on the amino acid sequence and base sequence information disclosed as NM__198899, insulin secretion regulation factor was synthesized. In brief, using two primers designed based on the base sequence information (SEQ ID NO: 1) obtained as above, thus T7 full-length 5' primer: 5'-TAA TAC GAC TCA CTA CTA TAG GGA GCC CACC ATGTGCAGCCGGGGG-3' (SEQ ID NO: 5) (the underlined part corresponds to nucleotides 1-15 of SEQ ID NO: 1), and full-length 3'-primer: 5'-TCATAATTCCTCATG-3' (SEQ ID NO: 6) (the underlined part corresponds to nucleotides 4656-4652 of SEQ ID NO: 1), cDNA (full-length) of insulin secretion regulation factor was amplified. Also using two primers designed based on the base sequence information (SEQ ID NO: 1), thus T7 C-terminal 5' primer: 5'-TAA TAC GAC TCA CTA CTA TAG GGA GCC CAC C ATG ATCAATATTTTCTCT-3' (SEQ ID NO: 7) (the underlined part corresponds to nucleotides 3766-3780 of SEQ ID NO: 1, nucleotides 1-15 of SEQ ID NO: 3), and full-length 3' primer (above), the gene of fragment at the C-terminal end of insulin secretion regulation factor was amplified. These amplified products were each introduced into vectors (pcDNA6, pGEX) to construct expression vectors. From the above PCR-amplified DNA fragment using an in vitro transcription & translation system (TNT Quick coupled transcription/translation system of Promega), a gene recombinant protein was generated in vitro. Also, by introducing the DNA inserted into the above two vectors into respective host cells (Escherichia coli), insulin secretion regulation factor (full-length protein) consisting of the amino acid sequence of SEQ ID NO: 2 and the C-terminal fragment of an insulin secretion regulation factor consisting of an amino acid sequence of SEQ ID NO: 4 were obtained. After fractionation with SDS-PAGE, this gel was stained to confirm the expression of the protein of interest.

(2) Binding Activity of Insulin Secretion Regulation Factor

Figure 2:
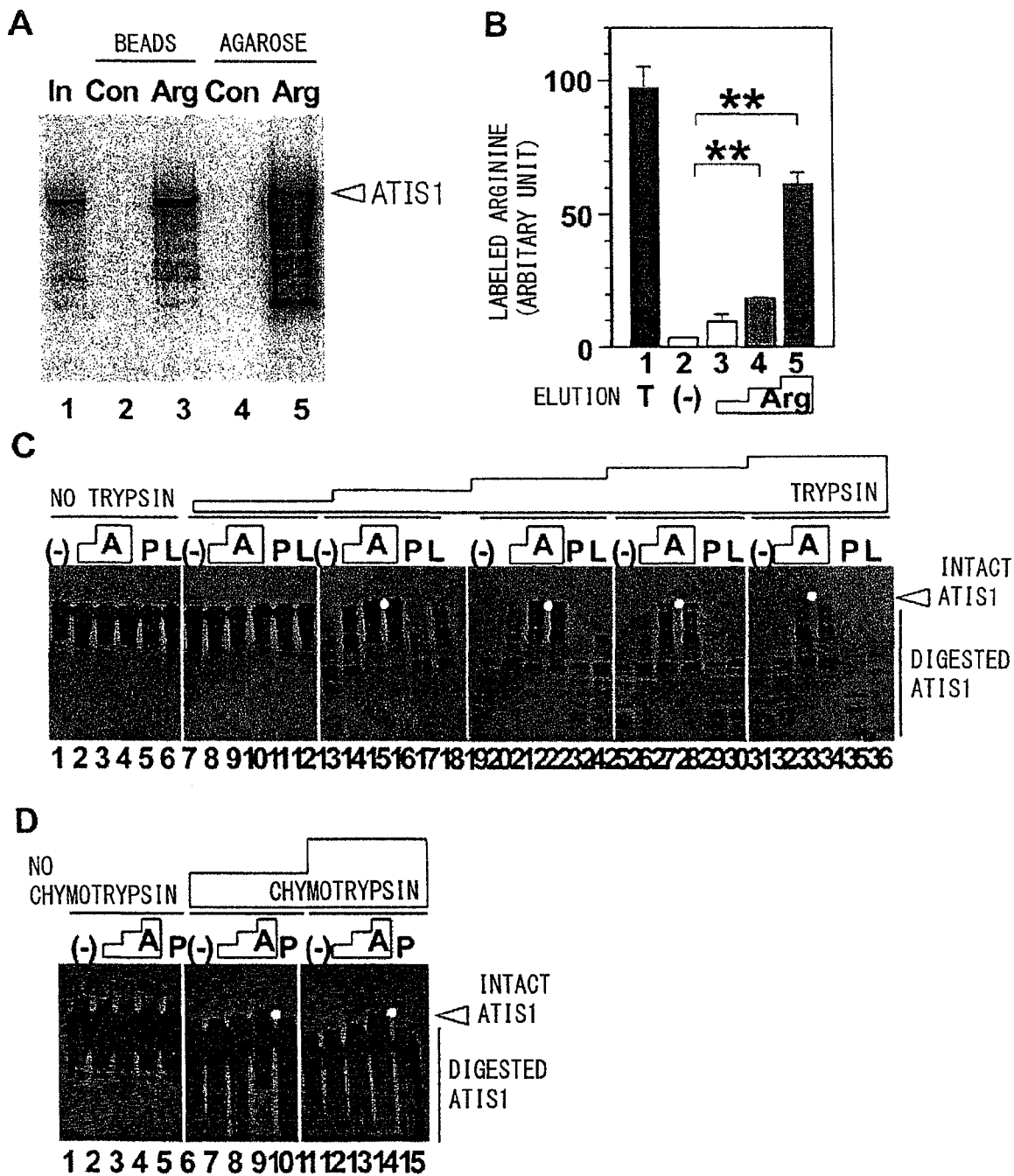
FIG. 2 shows the analytical result on the ability of an insulin secretion regulation factor for binding to arginine.

Using AME-immobilized magnetic nanobeads and arginine-immobilized agarose (manufactured by Sigma), the binding property of insulin secretion regulation factor to arginine was examined. First, in order to facilitate easy detection of insulin secretion regulation factor bound to arginine, insulin secretion regulation factor had been previously $^{35}$S-labelled. The $^{35}$S-labelled insulin secretion regulation factor sample was diluted with SDS-PAGE loading buffer (50 mM Tris-HCl, pH 6.8, 2% SDS, 100 mM β-mercaptoethanol, 10% glycerol, 0.01% bromophenol blue), and denatured at 95° C. for 5 minutes. The sample was developed on a 5-20% gradient precast gel (Wako Pure Chemical Industries, Ltd.), and electrophoresed using a DPE-1020 cassette electrophoresis unit (Daiichi) at 200 V for 60 minutes. As the control, non-AME-immobilized beads and arginine-free agarose were used. After electrophoresis, the gel was silver-stained and the result is shown in FIG. 2A. As can be seen in lane 3 of FIG. 2A, the insulin secretion regulation factor that was captured by the AME-immobilized magnetic beads appeared as one band (indicated as "ATIS1"), and the insulin secretion regulation factor of the present invention can be seen to bind to arginine. Also, when the arginine-immobilized agarose was used, a plurality of bands other than ATIS1 appeared, which are believed to indicate nonspecific decomposition of ATIS1 (lane 5). On the other hand, the control arginine-free beads and agarose, no insulin secretion regulation factor was detected (lanes 2 and 4, respectively), but in the AME-immobilized magnetic nanobeads and arginine-immobilized agarose, intense bands were detected (lanes 3 and 5, respectively). Lane 1 shows the electrophoresis of a sample that was not captured by the beads or agarose.

Next, a competitive inhibition experiment of insulin secretion regulation factor and arginine was conducted. After mixing radiolabelled arginine with insulin secretion regulation factor, non-radiolabelled (cold) arginine was allowed to inhibit competitively in a concentration-dependent manner, and the disconnected radiolabelled arginine was counted (FIG. 2B). As a result, as the concentration of cold arginine increases, the radiolabelled arginine that had been bound was disconnected from insulin secretion regulation factor, resulting in an increase in counts.

Furthermore, changes in sensitivity to arginine by digestive enzymes (trypsin treatment (FIG. 2C) or chymotrypsin treatment (FIG. 3D)) of insulin secretion regulation factor was examined. First, radiolabelled insulin secretion regulation factor was mixed with 100 μM of arginine on ice, and then treated for 10 minutes with varying concentrations of trypsin (0, 0.06, 0.32, 0.6, 2.0, 20 μg/mL) or chymotrypsin (0, 0.6, 2.0 μg/mL) on ice to partially digest it. The SDS-PAGE loading buffer was added and boiled for 5 minutes to stop enzyme treatment. Then, the digested product was separated on SDS-PAGE. After drying, the gel was subjected to autoradiography to visualize the radiolabelled digested product. As a result, when treated with trypsin, in the case of A (in the presence of Arginine) compared with the case of the absence or the presence of P (Phenylalanin)) or L (Leucine), significant resistance to trypsin partial digestion was noted. Also, when treated with chymotrypsin, in the case of A (in the presence of Arginine) compared with the case of the absence or the presence of P (Phenylalanine) or L (Leucine), significant resistance to chymotrypsin partial digestion was noted. The above results confirmed that the insulin secretion regulation factor of the present invention binds to arginine.

Figure 3:
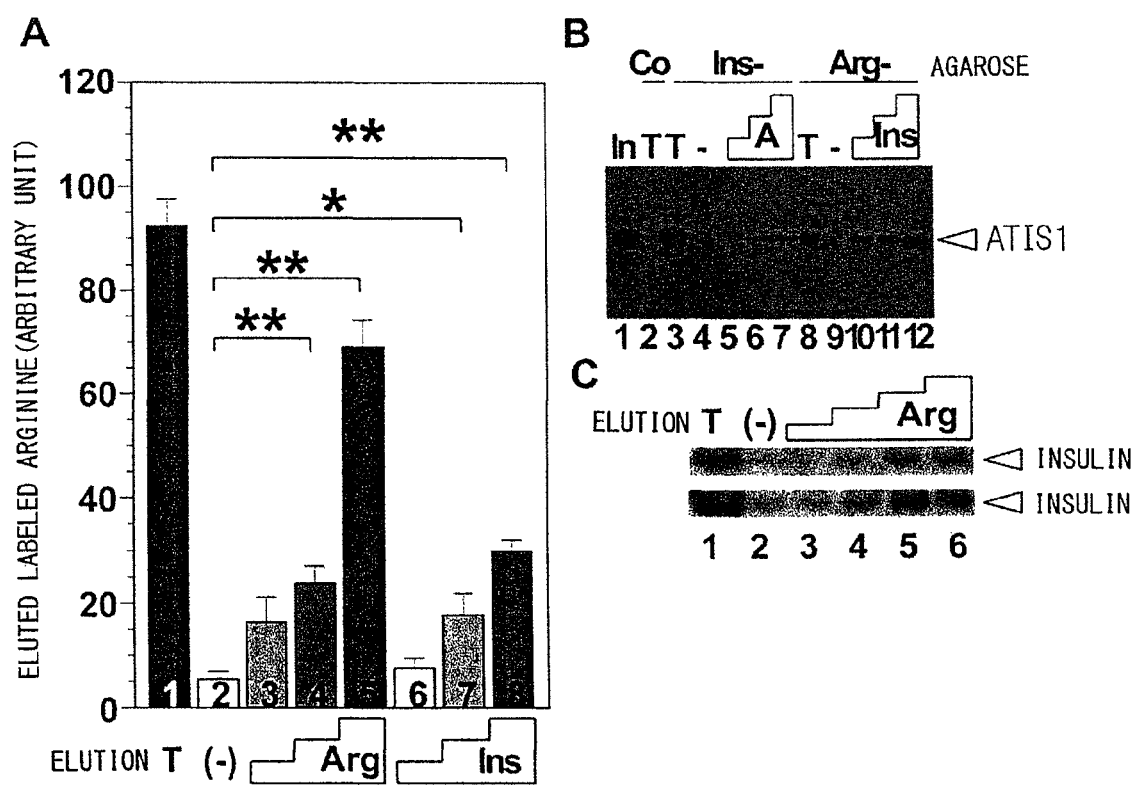
FIG. 3 shows the property of insulin secretion regulation factor-arginine binding and its competitive inhibition.

Next, competitive inhibition of insulin secretion regulation factor and insulin or arginine was examined. FIG. 3A shows the result of arginine or insulin competitive inhibition when radiolabelled arginine was used. After binding radiolabelled arginine and insulin secretion regulation factor, cold arginine or insulin was added for competitive inhibition, and the radiolabelled arginine that was disconnected from the insulin secretion regulation factor was counted in a manner similar to FIG. 2B. The results showed that as the concentration of cold arginine and insulin increased, the amount of disconnected radiolabelled arginine increased, indicating that insulin secretion regulation factor binds to arginine and insulin. Also, in FIG. 3B, radiolabelled insulin secretion regulation factor was allowed to bind to insulin-immobilized agarose or arginine-immobilized agarose (both manufactured by Sigma), and the radiolabelled insulin secretion regulation factor that was disconnected with arginine or insulin was subjected to electrophoresis, followed by silver staining. This revealed that arginine and insulin compete with each other for the inhibition of insulin secretion regulation factor. In FIG. 3C, after mixing insulin and insulin secretion regulation factor, arginine was added, and insulin disconnected from insulin secretion regulation factor was detected. It can be seen that depending on the amount of arginine added, the amount of disconnected insulin increases.

The above results strongly suggest that insulin secretion regulation factor can be competitively bound to arginine and insulin, and that the mechanism of arginine-induced insulin secretion is as described in FIG. 1.

Working Example 2

Regulation of Arginine-Induced Insulin Secretion by Insulin Secretion Regulation Factor in NIT-1 Cells Using NIT-1 cells in which insulin secretion regulation factor was forcibly expressed, the activity of arginine-induced insulin secretion was measured. In brief, after culturing about $1\times10^5$ NIT-1 cells (available from ATCC) in F12K medium (only arginine is absent from the normal F12 medium) containing no 10% FCS (fetal calf serum) beforehand, an expression vector having integrated therein a gene encoding the insulin secretion regulation factor obtained in Working Example 1 was transfected into NIT-1 cells using Lipofectamine 2000 (Invitrogen). Then, 0.1, 0.2, 0.6, 2.0, and 20 mM of arginine was added to this culture system, cultured for 10 minutes, the medium was recovered, and the amount of insulin secreted per unit time was determined using Shibayagi Co., Ltd.'s Levis insulin measurement ELISA kit. The result is shown in FIG. 4. The line graph with open circles represents changes in the amount of arginine-induced insulin secretion by wild type NIT-1 cells having no forced expression of insulin secretion regulation factor and having the normal expression level. In wild type cells, depending on arginine concentration, insulin secretion is promoted. On the other hand, in the NIT-1 cells (ATIS1-NIT-1 in the figure) indicated by a line graph with closed circles and having the forced expression of insulin secretion regulation factor, insulin is not secreted at arginine concentration up to 0.6 mM, and insulin secretion was promoted similarly to the wild type cells by arginine at excess amounts of 2.0 mM or more (FIG. 4). The result demonstrates that the insulin secretion regulation factor of the present invention has a function of negatively regulating insulin secretion, and thus by comparing with wild type cells that express no insulin secretion regulation factor, the cell system can be used in screening of a substance that restores insulin secretion.

Working Example 3

Insulin Secretion in Mice in which Insulin Secretion Regulation Factor was Forcibly Expressed Generally, blood arginine concentration in mice and humans is the highest at about 200 μM immediately after food intake, and thereafter it gradually decreases with time of fasting to about 50 μM. The result observed in Working Example 2 that immediately after food intake insulin secretion is low due to the forced expression of insulin secretion regulation factor, whereas at some time after food intake insulin secretion would become equal to that in the wild type was reproduced, as described below, in mice in which insulin secretion regulation factor was forcibly expressed. First, mice that express insulin secretion regulation factor in the pancreatic β cells were generated. In brief, a vector in which insulin secretion regulation factor was conjugated downstream to the rat insulin promoter was generated based on pGS vector (Imai, T., Jiang, M., Chambon, P. & Metzger, D., Impaired adipogenesis and Lipolysis in the mouse upon Cre-ERT2-mediated selective ablation of RXR alpha in adipocytes., Proc. Natl. Acad. Sci. U.S.A., 98: 224-228, 2001), injected into a fertilized egg, and thus the so-called transgenic mice were generated in the conventional method (F0 mice). DNA was extracted from the tail of F0 mice, and genotyping was carried out for the presence of transgene. Transgene-positive mice were crossed with wild type B6 mice to obtain F1 mice. Furthermore, genotyping of the F1 mice was also carried out, and only positive mice were further crossed with B6 mice. By repeating, F6 mice were analyzed. Primers used in genotyping were forward primer: 5'-GGC AAA GTT TTC AGG GTG TTG TT-3' (SEQ ID NO: 8), and reverse primer: 5'-TTA GCA GAG GGG CCC GGT TTG GAC TCA GAG-3' (SEQ ID NO: 9). It was confirmed by RT-PCR that F6 mice expressed the transgene specifically in the pancreas (data not shown). The primers used are forward primer: 5'-GGA TCG ATC CTG AGA ACT TC-3' (SEQ ID NO: 10), and reverse primer: 5'-CAG CAG AAG GCT CTC CAG AGT GTC-3' (SEQ ID NO: 11), as well as forward primer: 5'-GGA TCG ATC CTG AGA ACT TC-3' (SEQ ID NO: 12), and reverse primer: 5'-GCT AAG AAC TCA CTG GCT TCC AGC-3' (SEQ ID NO: 13).

Using the above generated mice (208) in which insulin secretion regulation factor was forcibly expressed in the pancreatic β cells, insulin secretion was analyzed (FIG. 5). Immediately after food re-intake, blood was drawn from mice at 2 hours and 8 hours of fasting, and blood insulin concentration was determined using Shibayagi Co., Ltd.'s Levis insulin measurement ELISA kit. As a result, immediately after food re-intake, and at 2 hours of fasting, insulin secretion ability was significantly decreased compared to wild type mice, whereas at 8 hours of fasting no difference was found from that in wild type mice. It can be seen from this result that the insulin secretion regulation factor of the present invention has a function of negatively regulating insulin secretion even at the animal level, and by comparing with wild type animals expressing no insulin secretion regulation factor, this animal system can be used for screening a substance that restores insulin secretion.

Working Example 4

Validation of Screening Method of Insulin Secretion-Promoting Substance Using NIT-1 Cells in which Insulin Secretion Regulation Factor was Forcibly Expressed Using NIT-1 cells in which insulin secretion regulation factor was forcibly expressed, the method of the present invention for screening an antidiabetic drug was validated. The compounds used in the validation were arginine, purified naturally occurring drupanin (Dru), purified naturally occurring baccharin (Bac), and chemically synthesized baccharin (sBac). Among them, drupanin and baccharin are both known as the main ingredient of propolis produced in Brazil (see Tani, H., et al., Inhibitory activity of Brazilian green propolis components and their derivatives on the release of cyc-leukotriens., Bioorg. Med. Chem., 18:151-157, 2010). On the other hand, propolis extracts are known to have an effect of improving insulin-dependent diabetes mellitus (type 1 diabetes mellitus) (for example, Japanese Unexamined Patent Publication No. 2010-37211). Thus, using a cell experimental system similar to that in Working Example 2, purified naturally occurring drupanin (Dru), purified naturally occurring baccharin (Bac), and chemically synthesized baccharin (sBac) were examined whether or not they promote insulin secretion similarly to arginine, and demonstrated that the screening method of the present invention is useful as described below. Dru and Bac were purified from Brazilian propolis (manufactured by Api), and sBac was synthesized by the present inventors by referring to the above article by Tani, et al.

Figure 6:
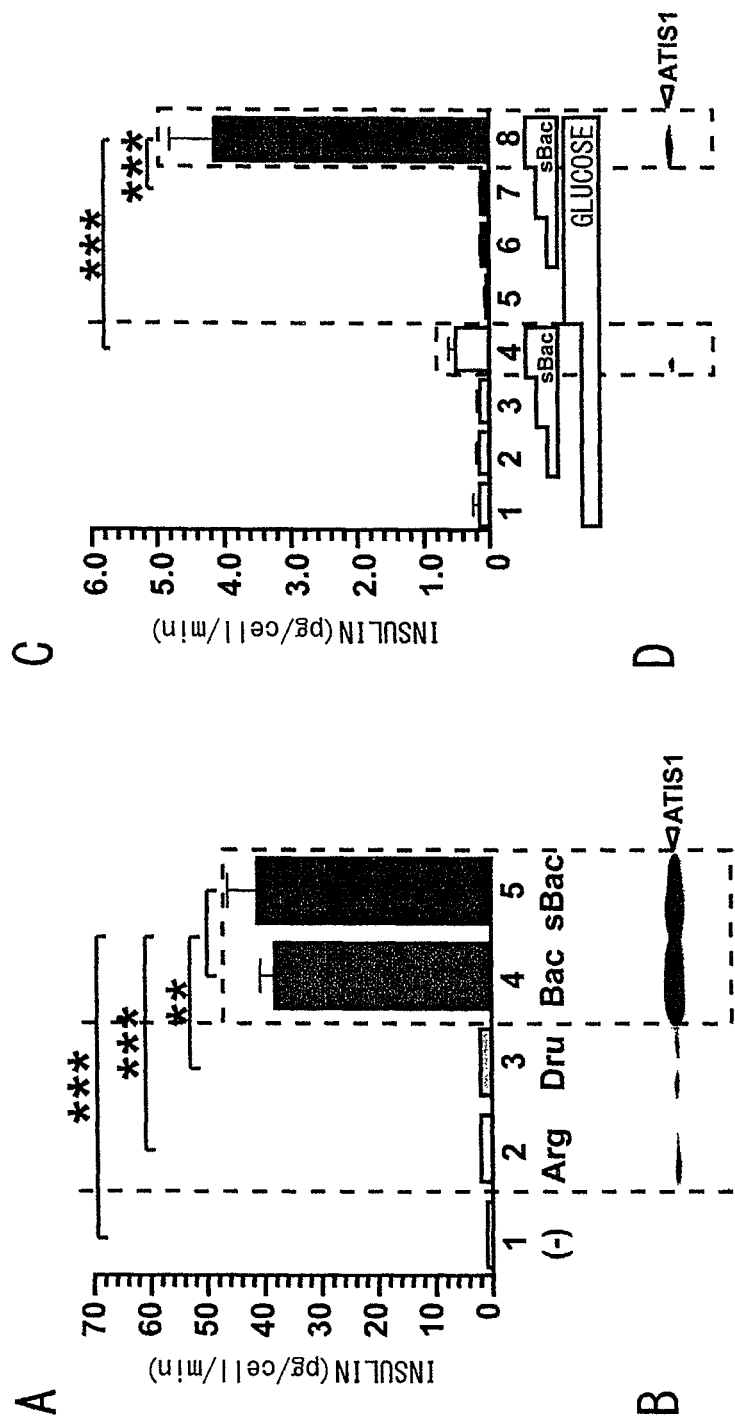
FIG. 6A shows the result of determining the amount of insulin secreted by the addition of arginine (Arg), purified naturally occurring drupanin (Dru), purified naturally occurring baccharin (Bac), and chemically synthesized baccharin (sBac) to NIT-1 cells in which insulin secretion regulation factor was forcibly expressed.
FIG. 6B is the result showing the interaction between each of the above insulin secretion promotion factors and an insulin secretion regulation factor (ATIS1).
FIG. 6C shows the effect of glucose concentration change in the culture medium on the insulin secretion-promoting activity of sBac.
FIG. 6D shows the result of interaction between sBac and an insulin secretion regulation factor (ATIS1).

To a culture system of NIT-1 cells transformed in a manner similar to Working Example 2, 10 mM each of arginine, drupanin (Dru), baccharin (Bac), and chemically synthesized baccharin (sBac) was added and cultured for 10 minutes. Then, each medium was recovered, and the amount of insulin secreted per unit time was determined using Shibayagi Co., Ltd.'s Levis insulin measurement ELISA kit. The residue is shown in FIG. 6A. Arginine (Arg) and drupanin (Drug) both secreted insulin to a similar degree (about 2 pg/cell/min (about 2000 fg/cell/min)). Thus, drupanin was also shown to be a substance that promotes insulin secretion to a similar degree to arginine. On the other hand, baccharin, whether naturally occurring or synthesized, was found to highly promote insulin secretion. From these experimental results, using the screening method of the present invention, drupanin and baccharin other than arginine were also identified as a candidate substance for promoting insulin secretion.

Next, it was confirmed that each insulin secretion-promoting substance interacts with insulin secretion regulation factor (ATIS1). The experiment was carried out in a manner similar to Working Example 1. In FIG. 6B, radiolabelled insulin secretion regulation factor was allowed to bind to insulin-immobilized agarose (manufactured by Sigma), and the radiolabelled insulin secretion regulation factor that was disconnected by Arg, Dru, Bac, or sBac was electrophoresed and then subjected to autoradiography. This has shown that each of Arg, Dru, Bac, and sBac competes with insulin for the inhibition of insulin secretion regulation factor. The shading of the bands of insulin secretion regulation factor (ATIS1) exhibited after autoradiography positively correlated with the amount of insulin secreted from the transformed NIT-1 cells by Arg, Dru, Bac, and sBac in FIG. 6A.

Also, changes in the amount of insulin secreted due to glucose concentration in the medium in the above cell culture system were examined. The experiment was conducted in two culture systems in which glucose concentration in the medium was 2.8 mM and 22.2 mM. As a result, when glucose concentration was low (1-4 in FIG. 6C), insulin secretion promotion was noted at the highest concentration of sBac (4), whereas at lower concentration of sBac, no changes in the amount of insulin secreted were observed (1-3). On the other hand, when glucose concentration was high (5-8 in FIG. 6C), almost no changes in insulin secretion were noted at low concentration of sBac (5-7), whereas insulin secretion was significantly promoted at the highest concentration of sBac. This suggests that sBac by binding to ATIS1 has an activity of promoting insulin secretion in a glucose-dependent manner. Furthermore, as in FIG. 6B, when the interaction between sBac and insulin secretion regulation factor (ATIS1) was examined, the shading of the band of ATIS1 exhibited after silver staining changed depending on the amount of sBac added, and positively correlated with the amount of insulin secreted from the transformed NIT-1 cells. As in FIG. 6C, insulin secretion and the amount of ATIS1 became the highest when glucose concentration was high and the sBac production was the highest (FIG. 6D).

Working Example 5

Validation of Glucose Concentration-Dependent Insulin Secretion-Promoting Activity of sBac Using Wild Type B6 Mice The glucose concentration-dependent insulin secretion-promoting activity of sBac shown in Working Example 4 was confirmed in vivo. More specifically, using wild type B6 mice, two lines of mice, mice after food re-intake and mice after 12 hours of fasting, were prepared, and blood insulin levels and blood glucose levels after the administration of various concentrations of sBac were determined. In any concentration of Bac administered in the fasted mice, no changes in blood insulin concentration and blood glucose concentration were noted relative to the control (vehicle alone) (FIG. 7A, open squares and open circles, respectively). In contrast, in mice having a high blood glucose concentration immediately after food re-intake, sBac administration led to increased blood insulin concentration depending on the sBac concentration, and furthermore, blood glucose concentration correspondingly decreased (FIG. 7A, closed circles and closed squares, respectively). These results suggested that, similarly to the result in Working Example 3 that was carried out in the cell culture system, sBac had glucose concentration-depending insulin secretion-promoting activity in a system employing mice as well.

To wild type B6 mice, sBac was administered at 85 nmol/30 g body weight (closed triangles) or 850 nmol/30 g body weight (close squares) to evaluate the effect of drug administration on the mice by determining changes in body weight with time. As can also been seen from FIG. 7B, as compared to the control (vehicle alone was administered), no mice that received sBac exhibited changes in body weight. Based on this, it can be said that sBac has no obesity-inducing activity as a side effect.

Figure 7:
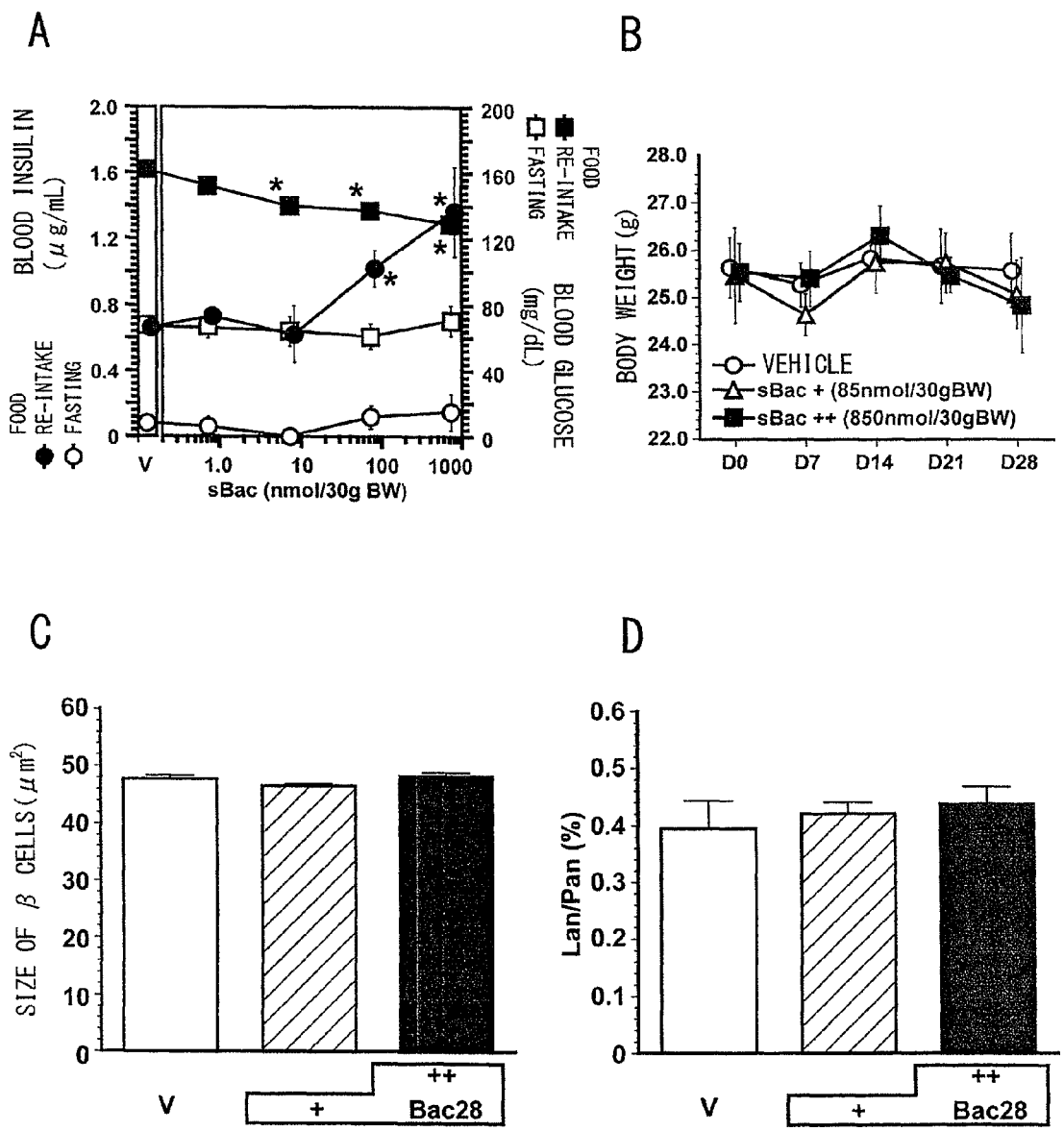
FIG. 7A shows the effect of sBac on insulin secretion in wild type B6 mice. Closed circles and closed squares represent changes in blood insulin concentration and glucose concentration, respectively, due to changes in the concentration of sBac administered to the mice after food re-intake. Open circles and open squares represent changes in blood insulin concentration and glucose concentration, respectively, due to changes in the concentration of sBac administered to the mice after fasting for 12 hours.
FIG. 7B shows changes with time in the body weight of the mice after the continuous administration of sBac for 4 weeks (28 days). Open circles represent the mice that received the vehicle alone, closed triangles represent the mice that received sBac at 85 nmol/30 g body weight, and closed squares represent the mice that received sBac at 850 nmol/30 g body weight.
FIG. 7C shows the size of Langerhans cells extracted from the mice 28 days after the administration of sBac at different concentrations.
FIG. 7D shows the ratio of Langerhans cells relative to the pancreas of the same mice.

Furthermore, on day 28 after sBac administration, the mice were sacrificed, and pancreatic β cells were removed from the mice. No changes in the size of pancreatic β cells were seen in any of the mice that received vehicle, 85 nmol/30 g body weight and 850 nmol/30 g body weight (FIG. 7C). Also, in the determination of the ratio of the Langerhans cells relative to the pancreas of each mouse, no changes in the ratio were noted in any mice (FIG. 7D). From these results, it can be said that there are no significant side effects on the pancreas (for example, killing of β cells).

Working Example 6

Interaction Between Insulin Secretion Regulation Factor and Amino Acid and Sugar It was examined whether amino acids other than arginine and sugars interact with insulin secretion regulation factor. The experiment was carried out similarly to Working Example 1. In brief, radiolabelled insulin secretion regulation factor was allowed to bind to arginine-immobilized agarose (manufactured by Sigma), and the radiolabelled insulin secretion regulation factor that was disconnected by arginine (Arg), ornithine (Orn), lysine (Lys), phenylalanine (Phe), citrulline (Cit), glutamine (Gln), Glc (Glu), and UDP-glucose was electrophoresed and then the gel was silver stained (FIG. 8A). The amino acids that interacted with the insulin secretion regulation factor were ornithine and lysine in addition to arginine, and both are cationic amino acids known to have an insulin secretion-promoting activity. Since the insulin secretion-promoting activity is in the order of arginine>ornithine, lysine, it had an extremely high positive correlation with the binding activity with ATIS1. Phenylalanine, which is a non-cationic amino acid and promotes insulin secretion via sulfanyl urea receptor (SUR), did not bind to ATIS1 as expected. Also, citrulline, which is similar to arginine and ornithine but not cationic, is known to have no insulin secretion-promoting activity, and did not exhibit the ATIS1 binding activity, either. Thus, among various amino acids, only cationic amino acids having insulin secretion-promoting activity bound to ATIS1. On the other hand, with regard to interaction with sugar, interestingly, insulin secretion regulation factor was found to have a very high affinity with UDP-glucose than with glucose. Thus, the insulin secretion-promoting activity of UDP-glucose was confirmed in an in vivo system. Similarly to Working Example 5, wild type B6 mice were used. To mice after food re-intake, UPD-glucose was administered at 4.2, 12.5, and 37.5 (mg/30 g body weight), and blood insulin concentration was determined. As shown in FIG. 8B, in mice that received UPD-glucose, blood insulin concentration increased depending on the increased concentration. This suggested that UDP-glucose functions as insulin secretion promotion factor.

Industrial Applicability

According to the insulin secretion regulation factor of the present invention, there can be provided a simple screening method for obtaining a substance useful as a antidiabetic drug (specifically insulin secretion-promoting drug) that can control blood sugar within the normal range.

All of the publications and patent documents cited herein are entirely incorporated herein by reference. The specific embodiments of the present invention were explained for the purpose of illustration, but it will be apparent to a person skilled in the art that various modifications can be made without departing from the spirit and scope of the present invention.

The invention claimed is:

1. A screening method which comprises selecting a test substance having an activity of binding to insulin secretion regulation factor, based on the activity of the test substance to bind to the insulin secretion regulation factor, as a candidate substance for use in a drug for treating or preventing diabetes mellitus, said method comprising the steps of:
   (a) preparing cultured cells in which, as insulin secretion regulation factor, the following protein:
      (i) a protein comprising an amino acid sequence represented by SEQ ID NO: 2 or SEQ ID NO: 4; or
      (ii) a protein comprising an amino acid sequence in which one or several amino acids are deleted, substituted or added in an amino acid sequence represented by SEQ ID NO: 2 or SEQ ID NO: 4 and negatively regulating insulin secretion was forcibly expressed;
   (b) culturing the cultured cells prepared in step (a) to express the protein;
   (c) bringing the test substance into contact with the protein prepared in step (b); and
   (d) selecting the test substance that bound to the protein as a candidate substance for use in a drug for treating or preventing diabetes mellitus.

2. The screening method according to claim 1, wherein the protein in the above step (a) is (i) a protein consisting of an amino acid sequence represented by SEQ ID NO: 2 or SEQ ID NO: 4; or (ii) a protein consisting of an amino acid sequence in which one or several amino acids are deleted, substituted or added in an amino acid sequence represented by SEQ ID NO: 2 or SEQ ID NO: 4 and negatively regulating insulin secretion.

* * * * *

SEQUENCE LISTING

```
<160> NUMBER OF SEQ ID NOS: 13

<210> SEQ ID NO 1
<211> LENGTH: 4656
<212> TYPE: DNA
<213> ORGANISM: Mouse

<400> SEQUENCE: 1
atgtgcagcc gggggatgc gaacactgcg gatgccgcgg ctgcgcggcg ggtgacaggg        60
ctccgttaca acatgagact cctgattgca ctggccttac cgtgcctgtt ttccttagca      120
```

-continued

```
gaagccaatt caaaagccat taccacctct ctcaccacaa agtggttttc tgccccactg    180
ctgctggaag ccagtgagtt cttagcagaa gacagtcaag agaaattttg gagttttgta    240
gaagccactc aaaacattgg atcatcagat catcacgata ctgatcactc ctattacgat    300
gccgtattgg aagctgcgtt tcgcttcctg tccctctgc agcagaattt gttgaagttt     360
tgtctctctc tccgttccta ctcagcctca attcaagcct tccagcagat agcagttgac    420
gagcctccac cagaagggtg caagtcgttt ctctcagtgc atggaaagca gacttgtgat    480
ctagacactc tggagagcct tctgctgact gccgctgaca gaccgaaacc attattgttc    540
aaaggagatc acagatatcc ctcatcaaat cctgagagtc cagtggtcat cctttattct    600
gagattggcc atgaagaatt ttctaatatt caccaccaac ttatatcaaa aagcaacgaa    660
ggcaaaatta attatgtatt ccgacattat atatctaatc ccagcaagga gccggtttac    720
ctttctggct atggagtgga actggcgatc aagagcacgg agtacaaggc caaggatgat    780
actcaggtga aaggaactga ggtaaatgcc acggtcatcg gggagagcga ccctattgat    840
gaagtgcagg gattcctctt tggaaaatta agagaactgt accccgcctt ggaaggacag    900
ctgaaagagt tccggaagca ccttgtggag agcaccaacg agatggcccc cctgaaagtc    960
tggcagctgc aagatctcag cttccagact gctgcccgaa tcttggctgc ttctggggca   1020
ttatctctgg tggtgatgaa ggacattagt cagaactttc ctaccaaggc cagagcaata   1080
acgaaaacgg ctgtgagcgc gcagcttaga gcggaagtgg aagagaacca gaagtatttc   1140
aagggaacta taggattaca gcctggagac tcagcgctct tcatcaatgg acttcatatc   1200
gatttagaca cccaggatat attcagtcta tttgatacat tgaggaatga agcccgtgta   1260
atggagggtc tgcacaggct gggaatagaa ggcctttctc tacataatat tttgaagctg   1320
aacatccagc cctctgagac tgactacgca gtagacatca ggagtcctgc tatttcctgg   1380
gtcaacaacc tagaggtcga tagccgatat aactcatggc cttcaagctt acaggagtta   1440
ctccgcccca cgtttcctgg tgtcatacgg cagatcagaa agaacctgca taacatggtt   1500
ttcattatcg atcctgtaca cgagaccaca gccgagttga ttagcatcgc cgagatgttc   1560
ctcagcaatc acataccgct aaggattggt tttatctttg tggtcaatga ctctgaagat   1620
gttgatggga tgcaagatgc tggagtcgct gttctgagag cgtataatta tgtggctcag   1680
gaagtggatg ctatcacgc cttccagact ctcacacaga tctataacaa ggtgaggact   1740
ggagagacag tgaaagtgga gcacgtggtc agtgtcttgg agaagaagta cccgtacgtg   1800
gaagtgaata gcattctggg aattgattct gcttacgatc agaatcggaa ggaagcaaga   1860
ggctactatg agcagactgg agtaggcccc ctgcctgttg tcctgttcaa tggaatgccc   1920
tttgaaaagg agcagttaga cccggatgag ctggaaacca tcacaatgca caagatcttg   1980
gagacaacca ccttcttcca aagagctgtg tacttgggtg agctgtccca tgatcaagat   2040
gtggtagagt acatcatgaa tcagccaaat gttgttccaa gaatcaactc taggattctg   2100
acagctaagc gagagtatct ggacctaaca gcaagcaata ttttatgt ggatgacttt    2160 gccagatttt ctgccttgga ctctcggggc aagacggctg ctattgccaa cagtatgaac   2220
tatctgacga aaaaggaat gtcctccaag gaaatctatg atgattcttt tattagacca    2280 gtgactttt ggattgttgg agattttgat agcccttctg ggcggcagct actatatgat    2340
gccattaaac atcagaaaac cagtaacaat gttaggataa gtatgatcaa caatcccagc   2400
caagagatca gtgactcaag cacccccatc ttcagagcca tctgggcagc tctgcaaaca   2460
caggcctcca gctctgctaa gaacttcatc accaagatgg ccaaagagga gacggcagag   2520
```

-continued

| | |
|---|---|
| gccctggccg caggagtgga cattgcggaa ttctctgtcg ggggcatgga tgtcagtctt | 2580 |
| tttaaagagg tctttgagtc ttccagaatg gatttcattt tgtctcatgc cctgtactgc | 2640 |
| agggatgttc tgaagctgaa gaagggacag cgagtggtga tcagcaacgg aaggatcatt | 2700 |
| gggcctctgg aggacaatga gctcttcaac caagatgatt tccacctcct ggaaaatatc | 2760 |
| atcctgaaaa catcgggaca gaaaataaag tctcatatcc aacagcttcg agtagaagaa | 2820 |
| gacgtggcca gtgatttggt aatgaaggtg gatgctctcc tgtcagcaca acccaaagga | 2880 |
| gaggcgagga tcgagtacca gttctttgag gataaacaca gtgcaattaa gctgaagccc | 2940 |
| aaagaaggag agacatacta tgatgtggta gccgttgttg accctgtcac acgagaagca | 3000 |
| cagaggctcg ccccccttgct cttggttttg actcagctga taaacatgaa tctaagagta | 3060 |
| tttatgaatt gccaatccaa gctttccgac atgcctttaa aaagctttta ccgttacgtc | 3120 |
| ttagagccgg agatttcttt cactgcagac agcagctttg ctaagggacc gatagcaaag | 3180 |
| tttctggata tgccacagtc tccgctgttt actttgaatc tgaacacacc tgagagttgg | 3240 |
| atggtagaat ctgtcagaac accatatgat ctggataata tttatctaga agaggtggac | 3300 |
| agtatagtgg ctgctgagta tgagctggaa tatctgttac tagaaggtca ttgttacgac | 3360 |
| atcaccacag gccagccccc tcgaggacta cagttcactt taggaacttc agccaaccca | 3420 |
| acaattgtgg acacaattgt gatggccaat ctgggatatt ttcagctcaa agccaatccg | 3480 |
| ggagcctgga ttctgagact gaggaagggg cgctcagatg acatttatag gatctacagc | 3540 |
| catgatggta cagattcccc tcctgatgca aacgacgttg ttgtcatcct caataacttc | 3600 |
| aagagcaaga tcatcaaagt gaaggttcag aagaaggcag acatggctaa tgaagacttg | 3660 |
| ctgagtgatg ggacaaatga gaacgagtct ggattctggg actcattcaa gtggggcttc | 3720 |
| tcaggacaga aggctgaaga agtgaagcaa gataaagatg acataatcaa tatttctctct | 3780 |
| gttgcatctg gtcatctcta cgaaagattt cttcgcatca tgatgctctc agtcctgaag | 3840 |
| aataccaaga ctcctgtgaa gttctggttc ttgaagaact acttgtcccc cacatttaag | 3900 |
| gagtttatac cttacatggc caaaaaatac aatttccagt atgagcttgt tcagtacaaa | 3960 |
| tggccaaggt ggcttcacca gcagacggag aagcagcgaa tcatctgggg ctacaagatc | 4020 |
| ctcttcctgg acgtgctttt cccgctggtt gttgacaagt tcctctttgt ggatgctgat | 4080 |
| cagattgtac ggacagatct gaaggagtta agagatttca atttggatgg tgcgccttac | 4140 |
| ggttacactc ccttctgcga cagcaggaga gagatggatg ctaccgctt ctggaagtca | 4200 |
| gggtactggg ccagtcattt ggctggacga aagtatcaca tcagtgcgct gtatgtcgtg | 4260 |
| gatctgaaga agtttaggaa aatagctgct ggagacagac tcaggggaca gtaccaaggt | 4320 |
| ctgagccagg atcccaacag tctttcaaat cttgatcaag atttgcccaa taacatgatc | 4380 |
| catcaggtgc caatcaaatc gctccctcag gaatggcttt ggtgtgaaac gtggtgtgat | 4440 |
| gacgcctcta agaagcgggc aaagaccatc gacctgtgta taatcccat gactaaggag | 4500 |
| cccaaactgg aggctgccgt gcggatcgtc cctgagtggc aagactacga ccaggagatc | 4560 |
| aagcagctgc agaccctctt ccaagaggag aaggagctgg ggaccctgca tacagaggag | 4620 |
| acgcaggaag gctctcagaa gcatgaggaa ttatga | 4656 |

<210> SEQ ID NO 2
<211> LENGTH: 1551
<212> TYPE: PRT
<213> ORGANISM: Mouse

```
<400> SEQUENCE: 2

Met Cys Ser Arg Gly Asp Ala Asn Thr Ala Asp Ala Ala Ala Ala Arg
1               5                   10                  15
Arg Val Thr Gly Leu Arg Tyr Asn Met Arg Leu Leu Ile Ala Leu Ala
            20                  25                  30
Leu Pro Cys Leu Phe Ser Leu Ala Glu Ala Asn Ser Lys Ala Ile Thr
        35                  40                  45
Thr Ser Leu Thr Thr Lys Trp Phe Ser Ala Pro Leu Leu Leu Glu Ala
    50                  55                  60
Ser Glu Phe Leu Ala Glu Asp Ser Gln Glu Lys Phe Trp Ser Phe Val
65                  70                  75                  80
Glu Ala Thr Gln Asn Ile Gly Ser Ser Asp His Asp Thr Asp His
                85                  90                  95
Ser Tyr Tyr Asp Ala Val Leu Glu Ala Ala Phe Arg Phe Leu Ser Pro
                100                 105                 110
Leu Gln Gln Asn Leu Leu Lys Phe Cys Leu Ser Leu Arg Ser Tyr Ser
            115                 120                 125
Ala Ser Ile Gln Ala Phe Gln Gln Ile Ala Val Asp Glu Pro Pro Pro
        130                 135                 140
Glu Gly Cys Lys Ser Phe Leu Ser Val His Gly Lys Gln Thr Cys Asp
145                 150                 155                 160
Leu Asp Thr Leu Glu Ser Leu Leu Leu Thr Ala Ala Asp Arg Pro Lys
                165                 170                 175
Pro Leu Leu Phe Lys Gly Asp His Arg Tyr Pro Ser Ser Asn Pro Glu
            180                 185                 190
Ser Pro Val Val Ile Leu Tyr Ser Glu Ile Gly His Glu Glu Phe Ser
        195                 200                 205
Asn Ile His His Gln Leu Ile Ser Lys Ser Asn Glu Gly Lys Ile Asn
    210                 215                 220
Tyr Val Phe Arg His Tyr Ile Ser Asn Pro Ser Lys Glu Pro Val Tyr
225                 230                 235                 240
Leu Ser Gly Tyr Gly Val Glu Leu Ala Ile Lys Ser Thr Glu Tyr Lys
                245                 250                 255
Ala Lys Asp Asp Thr Gln Val Lys Gly Thr Glu Val Asn Ala Thr Val
            260                 265                 270
Ile Gly Glu Ser Asp Pro Ile Asp Glu Val Gln Gly Phe Leu Phe Gly
        275                 280                 285
Lys Leu Arg Glu Leu Tyr Pro Ala Leu Glu Gly Gln Leu Lys Glu Phe
    290                 295                 300
Arg Lys His Leu Val Glu Ser Thr Asn Glu Met Ala Pro Leu Lys Val
305                 310                 315                 320
Trp Gln Leu Gln Asp Leu Ser Phe Gln Thr Ala Ala Arg Ile Leu Ala
                325                 330                 335
Ala Ser Gly Ala Leu Ser Leu Val Val Met Lys Asp Ile Ser Gln Asn
            340                 345                 350
Phe Pro Thr Lys Ala Arg Ala Ile Thr Lys Thr Ala Val Ser Ala Gln
        355                 360                 365
Leu Arg Ala Glu Val Glu Glu Asn Gln Lys Tyr Phe Lys Gly Thr Ile
    370                 375                 380
Gly Leu Gln Pro Gly Asp Ser Ala Leu Phe Ile Asn Gly Leu His Ile
385                 390                 395                 400
Asp Leu Asp Thr Gln Asp Ile Phe Ser Leu Phe Asp Thr Leu Arg Asn
                405                 410                 415
```

-continued

Glu Ala Arg Val Met Glu Gly Leu His Arg Leu Gly Ile Glu Gly Leu
            420                 425                 430

Ser Leu His Asn Ile Leu Lys Leu Asn Ile Gln Pro Ser Glu Thr Asp
        435                 440                 445

Tyr Ala Val Asp Ile Arg Ser Pro Ala Ile Ser Trp Val Asn Asn Leu
    450                 455                 460

Glu Val Asp Ser Arg Tyr Asn Ser Trp Pro Ser Ser Leu Gln Glu Leu
465                 470                 475                 480

Leu Arg Pro Thr Phe Pro Gly Val Ile Arg Gln Ile Arg Lys Asn Leu
                485                 490                 495

His Asn Met Val Phe Ile Ile Asp Pro Val His Glu Thr Thr Ala Glu
            500                 505                 510

Leu Ile Ser Ile Ala Glu Met Phe Leu Ser Asn His Ile Pro Leu Arg
        515                 520                 525

Ile Gly Phe Ile Phe Val Val Asn Asp Ser Glu Asp Val Asp Gly Met
    530                 535                 540

Gln Asp Ala Gly Val Ala Val Leu Arg Ala Tyr Asn Tyr Val Ala Gln
545                 550                 555                 560

Glu Val Asp Gly Tyr His Ala Phe Gln Thr Leu Thr Gln Ile Tyr Asn
                565                 570                 575

Lys Val Arg Thr Gly Glu Thr Val Lys Val Glu His Val Val Ser Val
            580                 585                 590

Leu Glu Lys Lys Tyr Pro Tyr Val Glu Val Asn Ser Ile Leu Gly Ile
        595                 600                 605

Asp Ser Ala Tyr Asp Gln Asn Arg Lys Glu Ala Arg Gly Tyr Tyr Glu
    610                 615                 620

Gln Thr Gly Val Gly Pro Leu Pro Val Val Leu Phe Asn Gly Met Pro
625                 630                 635                 640

Phe Glu Lys Glu Gln Leu Asp Pro Asp Glu Leu Glu Thr Ile Thr Met
                645                 650                 655

His Lys Ile Leu Glu Thr Thr Thr Phe Phe Gln Arg Ala Val Tyr Leu
            660                 665                 670

Gly Glu Leu Ser His Asp Gln Asp Val Val Glu Tyr Ile Met Asn Gln
        675                 680                 685

Pro Asn Val Val Pro Arg Ile Asn Ser Arg Ile Leu Thr Ala Lys Arg
    690                 695                 700

Glu Tyr Leu Asp Leu Thr Ala Ser Asn Asn Phe Tyr Val Asp Asp Phe
705                 710                 715                 720

Ala Arg Phe Ser Ala Leu Asp Ser Arg Gly Lys Thr Ala Ala Ile Ala
                725                 730                 735

Asn Ser Met Asn Tyr Leu Thr Lys Lys Gly Met Ser Ser Lys Glu Ile
            740                 745                 750

Tyr Asp Asp Ser Phe Ile Arg Pro Val Thr Phe Trp Ile Val Gly Asp
        755                 760                 765

Phe Asp Ser Pro Ser Gly Arg Gln Leu Leu Tyr Asp Ala Ile Lys His
    770                 775                 780

Gln Lys Thr Ser Asn Asn Val Arg Ile Ser Met Ile Asn Asn Pro Ser
785                 790                 795                 800

Gln Glu Ile Ser Asp Ser Ser Thr Pro Ile Phe Arg Ala Ile Trp Ala
                805                 810                 815

Ala Leu Gln Thr Gln Ala Ser Ser Ala Lys Asn Phe Ile Thr Lys
            820                 825                 830

-continued

```
Met Ala Lys Glu Glu Thr Ala Glu Ala Leu Ala Ala Gly Val Asp Ile
            835                 840                 845
Ala Glu Phe Ser Val Gly Gly Met Asp Val Ser Leu Phe Lys Glu Val
850                 855                 860
Phe Glu Ser Ser Arg Met Asp Phe Ile Leu Ser His Ala Leu Tyr Cys
865                 870                 875                 880
Arg Asp Val Leu Lys Leu Lys Lys Gly Gln Arg Val Val Ile Ser Asn
            885                 890                 895
Gly Arg Ile Ile Gly Pro Leu Glu Asp Asn Glu Leu Phe Asn Gln Asp
        900                 905                 910
Asp Phe His Leu Leu Glu Asn Ile Ile Leu Lys Thr Ser Gly Gln Lys
        915                 920                 925
Ile Lys Ser His Ile Gln Gln Leu Arg Val Glu Glu Asp Val Ala Ser
        930                 935                 940
Asp Leu Val Met Lys Val Asp Ala Leu Leu Ser Ala Gln Pro Lys Gly
945                 950                 955                 960
Glu Ala Arg Ile Glu Tyr Gln Phe Phe Glu Asp Lys His Ser Ala Ile
            965                 970                 975
Lys Leu Lys Pro Lys Glu Gly Glu Thr Tyr Tyr Asp Val Val Ala Val
            980                 985                 990
Val Asp Pro Val Thr Arg Glu Ala Gln Arg Leu Ala Pro Leu Leu Leu
        995                 1000                1005
Val Leu Thr Gln Leu Ile Asn Met Asn Leu Arg Val Phe Met Asn Cys
        1010                1015                1020
Gln Ser Lys Leu Ser Asp Met Pro Leu Lys Ser Phe Tyr Arg Tyr Val
1025                1030                1035                1040
Leu Glu Pro Glu Ile Ser Phe Thr Ala Asp Ser Ser Phe Ala Lys Gly
            1045                1050                1055
Pro Ile Ala Lys Phe Leu Asp Met Pro Gln Ser Pro Leu Phe Thr Leu
            1060                1065                1070
Asn Leu Asn Thr Pro Glu Ser Trp Met Val Glu Ser Val Arg Thr Pro
        1075                1080                1085
Tyr Asp Leu Asp Asn Ile Tyr Leu Glu Glu Val Asp Ser Ile Val Ala
        1090                1095                1100
Ala Glu Tyr Glu Leu Gly Tyr Leu Leu Leu Glu Gly His Cys Tyr Asp
1105                1110                1115                1120
Ile Thr Thr Gly Gln Pro Pro Arg Gly Leu Gln Phe Thr Leu Gly Thr
            1125                1130                1135
Ser Ala Asn Pro Thr Ile Val Asp Thr Ile Val Met Ala Asn Leu Gly
            1140                1145                1150
Tyr Phe Gln Leu Lys Ala Asn Pro Gly Ala Trp Ile Leu Arg Leu Arg
            1155                1160                1165
Lys Gly Arg Ser Asp Asp Ile Tyr Arg Ile Tyr Ser His Asp Gly Thr
        1170                1175                1180
Asp Ser Pro Pro Asp Ala Asn Asp Val Val Ile Leu Asn Asn Phe
1185                1190                1195                1200
Lys Ser Lys Ile Ile Lys Val Val Gln Lys Ala Asp Met Ala
            1205                1210                1215
Asn Glu Asp Leu Leu Ser Asp Gly Thr Asn Glu Asn Glu Ser Gly Phe
            1220                1225                1230
Trp Asp Ser Phe Lys Trp Gly Phe Ser Gly Gln Lys Ala Glu Glu Val
        1235                1240                1245
```

```
Lys Gln Asp Lys Asp Asp Ile Ile Asn Ile Phe Ser Val Ala Ser Gly
   1250                1255                1260

His Leu Tyr Glu Arg Phe Leu Arg Ile Met Met Leu Ser Val Leu Lys
1265                1270                1275                1280

Asn Thr Lys Thr Pro Val Lys Phe Trp Phe Leu Lys Asn Tyr Leu Ser
            1285                1290                1295

Pro Thr Phe Lys Glu Phe Ile Pro Tyr Met Ala Lys Lys Tyr Asn Phe
        1300                1305                1310

Gln Tyr Glu Leu Val Gln Tyr Lys Trp Pro Arg Trp Leu His Gln Gln
    1315                1320                1325

Thr Glu Lys Gln Arg Ile Ile Trp Gly Tyr Lys Ile Leu Phe Leu Asp
1330                1335                1340

Val Leu Phe Pro Leu Val Val Asp Lys Phe Leu Phe Val Asp Ala Asp
1345                1350                1355                1360

Gln Ile Val Arg Thr Asp Leu Lys Glu Leu Arg Asp Phe Asn Leu Asp
            1365                1370                1375

Gly Ala Pro Tyr Gly Tyr Thr Pro Phe Cys Asp Ser Arg Arg Glu Met
        1380                1385                1390

Asp Gly Tyr Arg Phe Trp Lys Ser Gly Tyr Trp Ala Ser His Leu Ala
    1395                1400                1405

Gly Arg Lys Tyr His Ile Ser Ala Leu Tyr Val Val Asp Leu Lys Lys
1410                1415                1420

Phe Arg Lys Ile Ala Ala Gly Asp Arg Leu Arg Gly Gln Tyr Gln Gly
1425                1430                1435                1440

Leu Ser Gln Asp Pro Asn Ser Leu Ser Asn Leu Asp Gln Asp Leu Pro
            1445                1450                1455

Asn Asn Met Ile His Gln Val Pro Ile Lys Ser Leu Pro Gln Glu Trp
        1460                1465                1470

Leu Trp Cys Glu Thr Trp Cys Asp Asp Ala Ser Lys Lys Arg Ala Lys
    1475                1480                1485

Thr Ile Asp Leu Cys Asn Asn Pro Met Thr Lys Glu Pro Lys Leu Glu
1490                1495                1500

Ala Ala Val Arg Ile Val Pro Glu Trp Gln Asp Tyr Asp Gln Glu Ile
1505                1510                1515                1520

Lys Gln Leu Gln Thr Leu Phe Gln Glu Glu Lys Glu Leu Gly Thr Leu
            1525                1530                1535

His Thr Glu Glu Thr Gln Glu Gly Ser Gln Lys His Glu Glu Leu
        1540                1545                1550

<210> SEQ ID NO 3
<211> LENGTH: 891
<212> TYPE: DNA
<213> ORGANISM: Mouse

<400> SEQUENCE: 3
atcaatattt tctctgttgc atctggtcat ctctacgaaa gatttcttcg catcatgatg      60
ctctcagtcc tgaagaatac caagactcct gtgaagttct ggttcttgaa gaactacttg     120
tcccccacat ttaaggagtt tatacccttac atggccaaaa aatacaattt ccagtatgag    180
cttgttcagt acaaatggcc aaggtggctt caccagcaga cggagaagca gcgaatcatc    240
tggggctaca agatcctctt cctggacgtg ctttttcccg ctggttgttga caagttcctc    300 tttgtggatg ctgatcagat tgtacggaca gatctgaagg agttaagaga tttcaatttg    360
gatggtgcgc cttacggtta cactcccttc tgcgacagca ggagagagat ggatggctac    420
```

```
cgcttctgga agtcagggta ctgggccagt catttggctg acgaaagta tcacatcagt      480 gcgctgtatg tcgtggatct gaagaagttt aggaaaatag ctgctggaga cagactcagg      540
ggacagtacc aaggtctgag ccaggatccc aacagtcttt caaatcttga tcaagatttg      600
cccaataaca tgatccatca ggtgccaatc aaatcgctcc ctcaggaatg ctttggtgt       660 gaaacgtggt gtgatgacgc tctaagaag cgggcaaaga ccatcgacct gtgtaataat       720
cccatgacta aggagcccaa actggaggct gccgtgcgga tcgtccctga gtggcaagac      780
tacgaccagg agatcaagca gctgcagacc ctcttccaag aggagaagga gctggggacc     840
ctgcatacag aggagacgca ggaaggctct cagaagcatg aggaattatg a              891
```

<210> SEQ ID NO 4
<211> LENGTH: 296
<212> TYPE: PRT
<213> ORGANISM: Mouse

<400> SEQUENCE: 4

```
Ile Asn Ile Phe Ser Val Ala Ser Gly His Leu Tyr Glu Arg Phe Leu
1               5                   10                  15

Arg Ile Met Met Leu Ser Val Leu Lys Asn Thr Lys Thr Pro Val Lys
            20                  25                  30

Phe Trp Phe Leu Lys Asn Tyr Leu Ser Pro Thr Phe Lys Glu Phe Ile
        35                  40                  45

Pro Tyr Met Ala Lys Lys Tyr Asn Phe Gln Tyr Glu Leu Val Gln Tyr
    50                  55                  60

Lys Trp Pro Arg Trp Leu His Gln Gln Thr Glu Lys Gln Arg Ile Ile
65                  70                  75                  80

Trp Gly Tyr Lys Ile Leu Phe Leu Asp Val Leu Phe Pro Leu Val Val
                85                  90                  95

Asp Lys Phe Leu Phe Val Asp Ala Asp Gln Ile Val Arg Thr Asp Leu
            100                 105                 110

Lys Glu Leu Arg Asp Phe Asn Leu Asp Gly Ala Pro Tyr Gly Tyr Thr
        115                 120                 125

Pro Phe Cys Asp Ser Arg Arg Glu Met Asp Gly Tyr Arg Phe Trp Lys
    130                 135                 140

Ser Gly Tyr Trp Ala Ser His Leu Ala Gly Arg Lys Tyr His Ile Ser
145                 150                 155                 160

Ala Leu Tyr Val Val Asp Leu Lys Lys Phe Arg Lys Ile Ala Ala Gly
                165                 170                 175

Asp Arg Leu Arg Gly Gln Tyr Gln Gly Leu Ser Gln Asp Pro Asn Ser
            180                 185                 190

Leu Ser Asn Leu Asp Gln Asp Leu Pro Asn Asn Met Ile His Gln Val
        195                 200                 205

Pro Ile Lys Ser Leu Pro Gln Glu Trp Leu Trp Cys Glu Thr Trp Cys
    210                 215                 220

Asp Asp Ala Ser Lys Lys Arg Ala Lys Thr Ile Asp Leu Cys Asn Asn
225                 230                 235                 240

Pro Met Thr Lys Glu Pro Lys Leu Glu Ala Ala Val Arg Ile Val Pro
                245                 250                 255

Glu Trp Gln Asp Tyr Asp Gln Glu Ile Lys Gln Leu Gln Thr Leu Phe
            260                 265                 270
```

Gln Glu Glu Lys Glu Leu Gly Thr Leu His Thr Glu Thr Gln Glu
    275                 280                 285

Gly Ser Gln Lys His Glu Glu Leu
    290                 295

<210> SEQ ID NO 5
<211> LENGTH: 46
<212> TYPE: DNA
<213> ORGANISM: Artificial Sequence
<220> FEATURE:
<223> OTHER INFORMATION: Oligonucleotide primer used in PCR

<400> SEQUENCE: 5
taatacgact cactactata gggagcccac catgtgcagc cggggg         46

<210> SEQ ID NO 6
<211> LENGTH: 15
<212> TYPE: DNA
<213> ORGANISM: Artificial Sequence
<220> FEATURE:
<223> OTHER INFORMATION: Oligonucleotide primer used in PCR

<400> SEQUENCE: 6
tcataattcc tcatg         15

<210> SEQ ID NO 7
<211> LENGTH: 49
<212> TYPE: DNA
<213> ORGANISM: Artificial Sequence
<220> FEATURE:
<223> OTHER INFORMATION: Oligonucleotide primer used in PCR

<400> SEQUENCE: 7
taatacgact cactactata gggagcccac catgatcaat attttctct         49

<210> SEQ ID NO 8
<211> LENGTH: 23
<212> TYPE: DNA
<213> ORGANISM: Artificial Sequence
<220> FEATURE:
<223> OTHER INFORMATION: Oligonucleotide primer used in PCR

<400> SEQUENCE: 8
ggcaaagttt tcagggtgtt gtt         23

<210> SEQ ID NO 9
<211> LENGTH: 30
<212> TYPE: DNA
<213> ORGANISM: Artificial Sequence
<220> FEATURE:
<223> OTHER INFORMATION: Oligonucleotide primer used in PCR

<400> SEQUENCE: 9
ttagcagagg ggcccggttt ggactcagag         30

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide primer used in PCR

<400> SEQUENCE: 10
ggatcgatcc tgagaacttc         20

```
<210> SEQ ID NO 11
<211> LENGTH: 24
<212> TYPE: DNA
<213> ORGANISM: Artificial Sequence
<220> FEATURE:
<223> OTHER INFORMATION: Oligonucleotide primer used in PCR

<400> SEQUENCE: 11
cagcagaagg ctctccagag tgtc                                          24

<210> SEQ ID NO 12
<211> LENGTH: 20
<212> TYPE: DNA
<213> ORGANISM: Artificial Sequence
<220> FEATURE:
<223> OTHER INFORMATION: Oligonucleotide primer used in PCR

<400> SEQUENCE: 12
ggatcgatcc tgagaacttc                                               20

<210> SEQ ID NO 13
<211> LENGTH: 24
<212> TYPE: DNA
<213> ORGANISM: Artificial Sequence
<220> FEATURE:
<223> OTHER INFORMATION: Oligonucleotide primer used in PCR

<400> SEQUENCE: 13
gctaagaact cactggcttc cagc                                          24
```